United States Patent [19]

Ertl et al.

[11] Patent Number: 6,019,978
[45] Date of Patent: *Feb. 1, 2000

[54] REPLICATION-DEFECTIVE ADENOVIRUS HUMAN TYPE 5 RECOMBINANT AS A VACCINE CARRIER

[75] Inventors: Hildegund C. J. Ertl, Villanova; James M. Wilson, Gladwyne, both of Pa.

[73] Assignees: The Wistar Institute of Anatomy and Biology; The Trustees of the University of Pennsylvania, both of Philadelphia, Pa.

[ * ] Notice: This patent is subject to a terminal disclaimer.

[21] Appl. No.: 08/973,223

[22] PCT Filed: Jun. 5, 1996

[86] PCT No.: PCT/US96/09495

§ 371 Date: Dec. 3, 1997

§ 102(e) Date: Dec. 3, 1997

[87] PCT Pub. No.: WO96/39178

PCT Pub. Date: Dec. 12, 1996

Related U.S. Application Data

[63] Continuation-in-part of application No. 08/461,837, Jun. 5, 1995, Pat. No. 5,698,202.
[60] Provisional application No. 60/000,078, Jun. 8, 1995.
[51] Int. Cl.[7] .......................... A61K 39/12; C12N 15/00; C12N 7/00; C07H 21/04
[52] U.S. Cl. ..................... 424/199.1; 424/204.1; 424/233.1; 435/235.1; 435/320.1; 536/23.72; 935/57; 935/65
[58] Field of Search .................. 424/199.1, 224.1, 424/233.1, 204.1; 435/235.1, 320.1, 32, 34, 57, 65; 536/23.72

[56] References Cited

U.S. PATENT DOCUMENTS 4,393,201  7/1983  Curtis et al. .

FOREIGN PATENT DOCUMENTS

| WO93/19191 | 9/1993 | WIPO . |
| WO94/12649 | 6/1994 | WIPO . |
| WO94/26914 | 11/1994 | WIPO . |
| WO94/28152 | 12/1994 | WIPO . |
| WO94/28938 | 12/1994 | WIPO . |
| WO95/00655 | 1/1995 | WIPO . |
| WO95/02697 | 1/1995 | WIPO . |

OTHER PUBLICATIONS

Jacobs et al, 1992, J. of Virology, vol. 66, No. 4, pp. 2086–2095, Apr. 1992.

Bett et al, 1994, PNAS,USA, vol. 91, pp. 8802–8806, Sep. 1994.

Greene W., 1993, Scientific American, pp. 99–105, Sep. 1993.

K. Kozarsky t al, "In Vivo Correction of Low Density Lipoprotein Receptor Deficiency in the Watanabe Heritable Hyperlipidemic Rabbit with Recombinant Adenoviruses", *J. Biol. Chem.*, 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics*, 19(5):449–458 (Sep., 1993) [Kozarsky II].

K. Kozarsky et al, "Gene Therapy: Adenovirus Vectors", *Curr. Opin. Genet. Devel.*, 3:499–503 (Mar., 1993) [Kozarsky III].

Y. Yang et al, "MHC Class I–Restricted Cytotoxic T Lymphocytes to Viral Antigens Destroy Hepatocytes in Mice Infected with E1–Deleted Recombinant Adenoviruses", *Immunity*, 1:433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA*, 91:4407–4411 (May, 1994) [Yang II].

Y. Yang et al, "Inactivation of E2a in Recombinant Adenoviruses Improves the Prospect for Gene Therapy in Cystic Fibrosis", *Nature Genetics*, 7:362–369 (Jul., 1994) [Yang III].

S. Ishibashi et al., "Hypercholesterolemia in Low Density Lipoprotein Receptor Knockout Mice and its Reversal by Adenovirus–mediated Gene Delivery", *J. Clin. Invest.*, 92:883–893 (Aug., 1993).

J. Engelhardt et al, "Ablation of E2A in Recombinant Adenoviruses Improves Transgene Persistence and Decreases Inflammatory Response in Mouse Liver", *Proc. Natl. Acad. Sci. USA*, 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.*, 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

M. Horwitz, "Adenoviridae and Their Replication", *Virology*, 2d edition, ed. B. N. Fields, Raven Press, Ltd., New York, Chapter 60, pp. 1679–1721 (1990).

(List continued on next page.)

*Primary Examiner*—Mary E. Mosher
*Assistant Examiner*—Ali R. Salimi
*Attorney, Agent, or Firm*—Howson and Howson

[57] ABSTRACT

A replication defective recombinant adenovirus is provided which contains a complete deletion of its E1 gene and at least a partial deletion of its E3 gene, said virus containing in the site of the E1 deletion a sequence comprising a non-adenovirus promoter directing the replication and expression of DNA encoding a heterologous protein from a disease-causing agent, which, when administered to a mammal in said recombinant virus, elicits a substantially complete protective immune response against the agent. Pharmaceutical and veterinary products containing the recombinant adenovirus are provided.

6 Claims, 6 Drawing Sheets

OTHER PUBLICATIONS

M. Boshart et al, "A Very Strong Enhancer is Located Upstream of an Immediate Early Gene of Human Cytomegalovirus", *Cell*, 41:521–530 (Jun., 1985).

K. Fisher et al, "Biochemical and Functional Analysis of an Adenovirus–Based Ligand Complex for Gene Transfer", *Biochem. J.*, 299:49–58 (Apr. 1, 1994).

T. Shenk et al, "Genetic Analysis fo Adenoviruses", *Current Topics in Microbiol. and Immunol.*, 111:1–39 (1984).

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

J. Logan et al, "Adenovirus Tripartite Leader Sequence Enhances Translation of mRNAs Late After Infection", *Proc. Natl. Acad. Sci. USA*, 81:3655–3659 (Jun., 1984).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

M. Eloit et al, "Construction of a Defective Adenovirus Vector Expressing the Pseudorabies Virus Glycoprotein gp50 and its Use as a Live Vaccine", *J. Gen. Virol.*, 71(10):2425–2431 (Oct., 1990).

S. Jacobs et al, "High–Level Expression of the Tick–Borne Encephalitis Virus NS1 Protein by Using an Adenovirus––Based Vector: Protection Elicited in a Murine Model", *J. Virol.*, 66:2086–2095 (Apr., 1992).

T. Ragot et al, "Replication–Defective Rcombinant Adenovirus Expressing the Epstein–Barr Virus (EBV) Envelope Glycoprotein gp340/220 Induces Protective Immunity Against EBV–induced Lymphomas in the Cottontop Tamarin", *J. Gen. Virol.*, 74(3):501–507 (Mar., 1993).

B. Brochier et al, "Towards Rabies Elimination in Belgium by Fox Vaccination Using a Vaccinia–Rabies Glycoprotein Recombinant Virus", *Vaccine*, 12(15):1368–1371 (Nov., 1994).

L. Prevec et al, "A Recombinant Human Adenovirus Vaccine Against Rabies", *J. Infect. Dis.*, 161:27–30 (Jan., 1990).

K. Charlton et al, "Oral Rabies Vaccination of Skunks and Foxes with a Recombinant Human Adenovirus Vaccine", *Arch. Virol.*, 123:169–179 (1992).

D. Johnson et al, "Abundant Expression of Herpes Simplex Virus Glycoprotein gB Using an Adenovirus Vector", *Virology*, 164:1–14 (1988).

R. Dewar et al, "Synthesis and Processing of Human Immunodeficiency Virus Type 1 Envelope Proteins Encoded by a Recombinant Human Adenovirus", *J. Virol.*, 63(1):129–136 (Jan., 1989).

A. Fooks et al, "High–Level Expression of the Measles Virus Nucleocapsid Protein by Using a Replication–Deficient Adenovirus Vector: Induction of an MHC–1–Restricted CTL Response and Protection in a Murine Model", *Virology*, 210:456–465 (1995).

V. Juillard et al, "Long–Term Humoral and Cellular Immunity Induced by a Single Immunization with Replication–Defective Adenovirus Recombinant Vector", *Eur. J. Immunol.*, 25:3467–3473 (Oct., 1995).

J–L. Imler, "Adenovirus Vectors as Recombinant Viral Vaccines", *Vaccine*, 13(13):1143–1151 (1995).

F. Graham et al, "Adenovirus–Based Expression Vectors and Recombinant Vaccines", *Biotechnology*, 20:363–390 (1992).

M. Levrero et al, "Defective and Nondefective Adenovirus Vectors for Expressing Foreign Genes in Vitro and in Vivo", *Gene*, pp. 195–202 (1990).

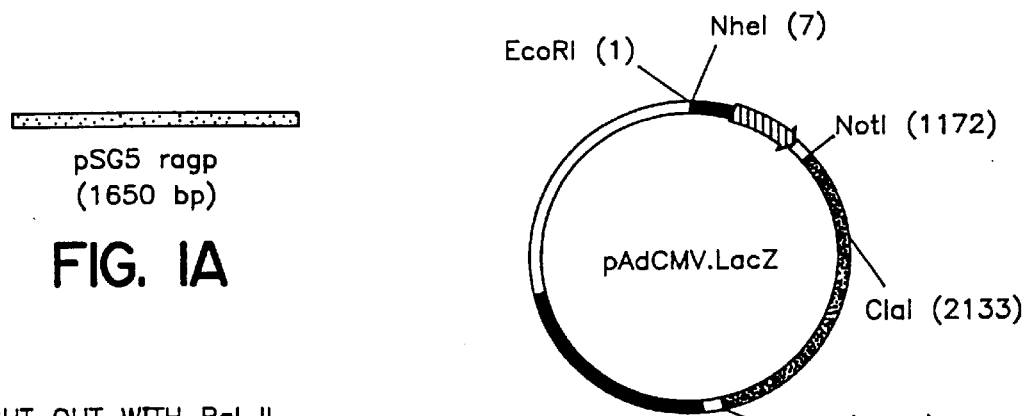
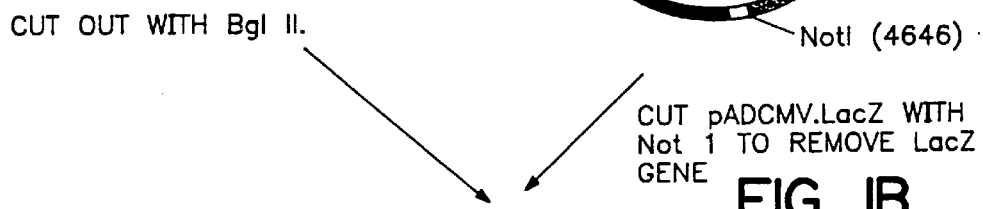
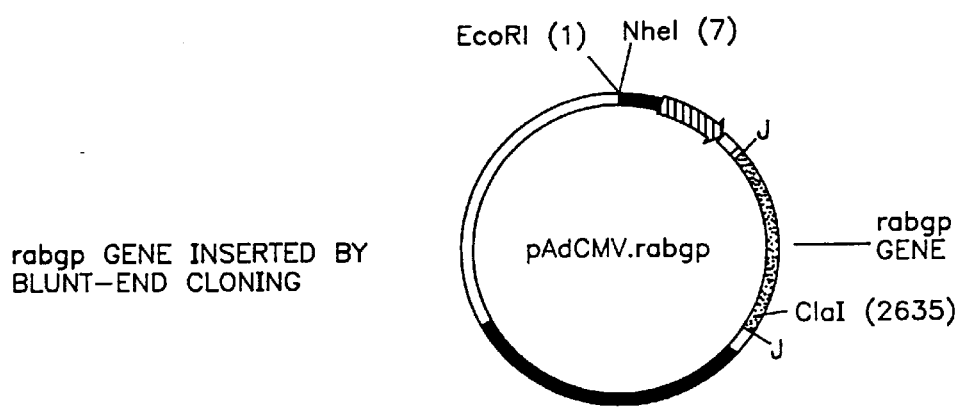
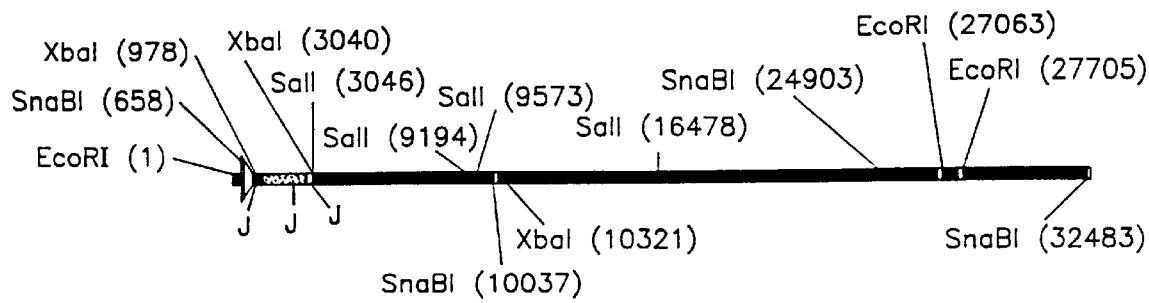

6,019,978

REPLICATION-DEFECTIVE ADENOVIRUS HUMAN TYPE 5 RECOMBINANT AS A VACCINE CARRIER

CROSS-REFERENCE TO RELATED APPLICATIONS

This is a rule 371 application based on the priority date of PCT/US96/09495, filed Jun. 6, 1996, which is a continuation in part of U.S. patent application Ser. No. 08/461,837, filed Jun. 5, 1995 and now U.S. Pat. No. 5,698,202; and is a continuation of provisional U.S. Patent Application Ser. No. 60/000,078, filed Jun. 8, 1995, now abandoned.

This invention was supported by the National Institutes of Health Grant Nos. NIH AI 33683-02 and NIH AI 27435-05. The United States government has certain rights in this invention.

FIELD OF THE INVENTION

This invention relates generally to recombinant adenoviruses as vaccine components, and more particularly, to the use of replication deficient adenoviruses as vaccine carriers, which induce protective immune responses in mammalian hosts.

BACKGROUND OF THE INVENTION

A replication competent, recombinant adenovirus (Ad) is an adenovirus with intact or functional essential genes, (i.e., E1a, E1b, E2a, E2b and E4). Such recombinant viruses containing a variety of inserted genes have been used as vaccine compositions with some success [see, e.g. Davis, U.S. Pat. No. 4,920,309].

One of these recombinant adenoviruses expressing the rabies G protein was shown to induce protective immunity in animals upon challenge with rabies virus [L. Prevac, *J. Infect. Dis.*, 161:27–30 (1990)]. However, doses above $10^6$ plaque-forming units (pfu) of this replication-competent virus were required to induce complete protection to viral challenge. Further, the use of these viruses in a live form capable of replicating in vivo is an undesirable attribute of a vaccine component.

In contrast, adenoviruses which have been made replication deficient by deletion of the Ad E1a and E1b genes have been used primarily for gene therapy protocols [See, e.g., Kozarsky and Wilson, *Curr. Opin. Genet. Dev.*, 3:499–503 91993); Kozarsky et al, *Som. Cell Mol. Genet.*, 19:449–458 (1993); see also, International Patent Application No. WO95/00655, published Jan. 5, 1995]. Such recombinant, replication deficient adenoviruses have been found to induce cell-mediated immune responses [Y. Yang et al, *Proc. Natl. Acad. Sci. USA*, 91:4407 (1994) and Y. Yang et al, *Immunity*, 1:433–442 (August 1994)] and neutralizing antibodies [T. Smith et al, *Gene Therapy*, 5:397 (1993); K. Kozarsky et al, *J. Biol. Chem.*, 269:13695 (1994)]. None of these articles relating to the use of recombinant replication deficient Ad in gene therapy have measured the induction of a protective immune response.

Others have described the insertion of a foreign gene into a replication-defective adenovirus for putative use as a vaccine [See, e.g. T. Ragot et al, *J. Gen. Virol.*, 74:501–507 (1993); M. Eliot et al, *J. Gen. Virol.*, 71:2425–2431 (1990); and S. C. Jacobs et al, *J. Virol.*, 66:2086–2095 (1992)]. Jacobs et al, cited above, describes a recombinant E1-deleted, E3 intact, Ad containing encephalitis virus protein NS1 under the control of a heterologous cytomegalovirus (CMV) promoter. When mice were immunized with the recombinant Ad vaccines and challenged with virus, Jacobs et al obtained only partial protection (at most a 75% protection) for an average survival of 15 days. Eliot et al, cited above, describe a recombinant E1-deleted, partially E3-deleted Ad with pseudorabies glycoprotein 50 inserted into the E1 deletion site under the control of a homologous Ad promoter. In rabbits and mice, after immunization and challenge, only partial protection was obtained (i.e., about one-third). Ragot et al, cited above, describe a recombinant E1-deleted, partially E3-deleted Ad with Epstein Barr virus glycoprotein gp340/220 inserted into the E1 deletion site under the control of a homologous Ad promoter. In marmosets (tamarins) after three high dose ($5 \times 10^9$ pfu, $1 \times 10^{10}$ pfu and $2 \times 10^{10}$ pfu), intramuscular immunizations and viral challenge, full protection was obtained.

For certain highly infectious diseases, such as rabies, there is a demand for an effective vaccine. Desirably, a vaccine should be effective at a low dosage to control the occurrence of side effects or to enable sufficient amounts of vaccine to be introduced into animals in the wild. Currently, a vaccinia rabies glycoprotein (VRG) vaccine is being used for oral wildlife immunization [B. Brochier et al, *Vaccine*, 12:1368–1371 (1994)]. However, doses above $10^6$ pfu are required to induce complete protection.

There thus remains a need in the art for a method of vaccinating against various disease states, and particularly rabies, which is safe and highly effective.

SUMMARY OF THE INVENTION

The inventors have surprisingly found compositions and methods of vaccinating a human and/or animal against a disease using an adenovirus defective vaccine composition, which produces a high level of protection upon administration of a low vaccine dose. For example, vaccination with a vaccine composition described herein, which is directed against rabies, has been found to require as little as a single dose of $10^4$ pfu of rabies vaccine vector to induce complete protection. This effect is also accomplished by administration routes other than the oral route.

Thus, in one aspect, the invention provides a replication-defective recombinant adenovirus (rAd) vaccine containing DNA encoding a selected heterologous protein from a disease-causing agent, which elicits a protective immune response against the agent. This recombinant adenovirus of the invention contains at least a partial, but functional, deletion of the Ad E3 gene. Further in the site of the E1a/E1b deletion which renders the Ad replication-defective, the recombinant virus contains a sequence comprising a non-adenovirus promoter directing the replication and expression of the DNA encoding the heterologous protein. For example, an exemplary rAd is Adrab.gp, which contains a rabies gp gene and is useful in a method for treating or preventing rabies.

In another aspect, the invention provides pharmaceutical and veterinary compositions which contain the rAd of the invention.

In still another aspect, the invention provides for the use of the rAd in the manufacture of the compositions described above.

In yet a further aspect, the invention provides a method of vaccinating a human or animal against disease comprising administering to said human or animal an effective amount of a replication-defective recombinant adenovirus vaccine containing DNA encoding a selected heterologous protein which elicits a protective immune response against an agent causing the disease. This adenovirus of the invention contains at least a partial, but functional, deletion of the Ad E3 gene. Further in the site of the E1a/E1b deletion which renders the Ad replication-defective, the recombinant virus contains a sequence comprising a non-adenovirus promoter directing the replication and expression of the DNA encoding the heterologous protein.

In another aspect, the present invention provides a method of preventing rabies infection in an animal comprising administering to the animal an effective amount of a recombinant replication-defective Adrab.gp adenovirus containing DNA encoding a rabies virus glycoprotein.

Other aspects and advantages of the present invention are described further in the following detailed description of the preferred embodiments thereof.

BRIEF DESCRIPTION OF THE DRAWINGS

FIG. 1A is a schematic representation of the 1650 bp rabies glycoprotein gene from Evelyn Rockitniki Abelseth strain excised from the pSG5.ragp plasmid by cleavage with BglII. The 1650 bp sequence spans nucleotide 1178 to 2827 of SEQ ID NO: 1.

FIG. 1B is a schematic map of the pAd.CMVlacZ (also known as H5.020CMVlacZ) plasmid, which contains adenovirus map units (m.u.) 0–1 as represented by the black bar at the top of the circular plasmid, followed by a cytomegalovirus enhancer/promoter (CMV enh/prom) represented by the striped arrow to the right of the black bar, a human betagalactosidase gene represented by the dark gray bar at the righthand side of the circular plasmid; a polyadenylation signal represented by the short white bar at the bottom of the circular plasmid, adenovirus m.u. 9–16 represented by the long black bar at the lower lefthand portion of the circular plasmid and plasmid sequences from plasmid pAT153 including an origin of replication and ampicillin resistance gene represented by the light gray bar at the upper lefthand portion of the circular plasmid. Restriction endonuclease enzymes are represented by conventional designations in this plasmid. NotI digestion removes the LacZ gene from this plasmid.

FIG. 1C is a schematic map of the plasmid pAdCMV.rabgp which results from blunt end cloning of the BglII fragment of pSG5.ragp to the larger NotI fragment of pAdCMV.lacZ. pAdCMV.rapgp is substantially similar to the pAd.CMVlacZ plasmid, but which contains the rabies glycoprotein sequence in place of the lacZ gene. pAdCMV.rapgp [SEQ ID NO: 1] contains adenovirus m.u. 0–1 as represented by the black bar at the top of the circular plasmid (nucleotides 12 to 364 of SEQ ID NO: 1); followed by a cytomegalovirus enhancer/promoter (CMV enh/prom) represented by the striped arrow to the right of the black bar [nucleotides 382 to 863 of SEQ ID NO: 1]; a rabies glycoprotein gene represented by the dotted bar at the righthand side of the circular plasmid (nucleotides 1178 to 2827 of SEQ ID NO: 1); a polyadenylation signal represented by the short white bar at the lower righthand portion of the circular plasmid [nucleotides 2836–3034 of SEQ ID NO: 1]; adenovirus m.u. 9–16 represented by the long black bar at the lower portion of the circular plasmid (nucleotides 3061 to 5524 of SEQ ID NO: 1); and plasmid sequences from plasmid pAT153 including an origin of replication and ampicillin resistance gene represented by the light gray bar at the upper lefthand portion of the circular plasmid (nucleotides 5525 to 8236 of SEQ ID NO: 1). Restriction endonuclease enzymes are represented by conventional designations. SEQ ID NO: 2 provides the rabies protein sequence encoded by the nucleotide sequence within pAdCMV.rabgp.

FIG. 1D is a schematic map of recombinant adenovirus Adrab.gp (also known as H5.020CMV.rab), which results from homologous recombination between pAdCMV.rabgp and Ad strain dl7001. Ad dl7001 is an Ad5 variant that carries an approximately 3 kb deletion of the Ad5 sequence (GenBank Accession No. M73260) between m.u. 78.4 through 86. The CMV/rabies glycoprotein/pA minicassette of pAd.CMVrab is inserted between deleted adenovirus m.u.1 and 9, with the remaining Ad5 m.u. 9–100 having the above-mentioned E3 gene deletion. Restriction endonuclease enzymes are represented by conventional designations.

DETAILED DESCRIPTION OF THE INVENTION

Figure 2:
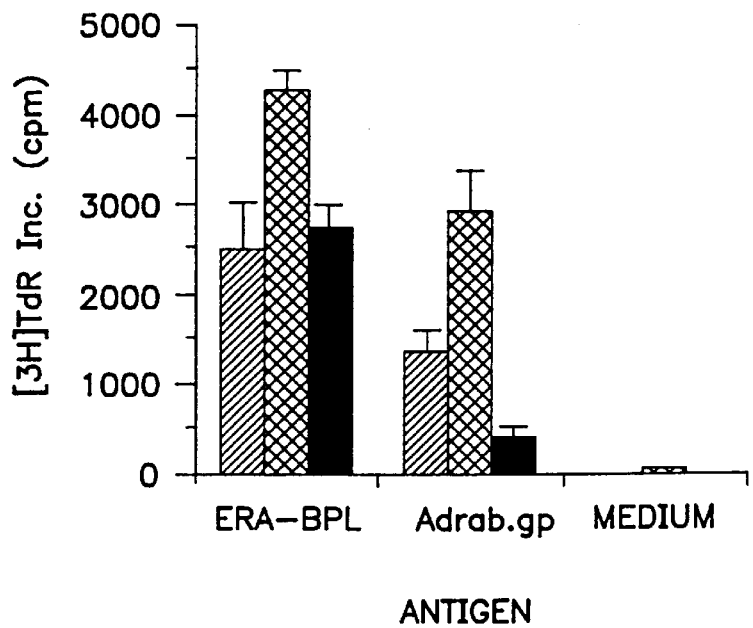
FIG. 2 is a bar graph plotting $^3$H-thymidine ([3H]TdR) incorporation, measured at counts per minute±standard deviation (cpm±SD), for irradiated splenocytes plated at $5 \times 10^5$ cells per well of a round bottom microtiter plate and incubated with 5 (diagonally striped), 1 (cross-hatched) or 0.2 (solid) μg/ml of betapropionolactone-inactivated Evelyn Rockitniki Abelseth rabies strain (ERA-BPL) or approximately 1 (diagonally striped), 0.1 (cross-hatched), and 0.01 (solid) pfu of Adrab.gp per cell or medium only as a negative control for 60 minutes at 37° C. As described in Example 2B, after cloned T cells were added, cells were pulsed two days later for 6 hours with $^3$H-thymidine, harvested and counted in a β-counter.

The present invention provides compositions and methods of effectively inducing a protective immune response to a disease agent. The compositions include a recombinant replication-defective adenovirus, and pharmaceutical and veterinary compositions containing the rAd. The rAd backbone was previously used for gene therapy. As discussed herein, the inventors have surprisingly found that use of such a recombinant Ad, described in detail below, provides substantially complete immune protection in vaccinates.

By "substantially complete" protection is meant when administered in an effective amount, the recombinant adenovirus presents an immunogenic protein in such a manner that a protective immune response is observed in substantially all vaccinates after a single administration. By "substantially all" is meant greater than 90% of the vaccinates. Unexpectedly, the recombinant vaccine permits successful vaccination with very few booster administrations. Also unexpectedly, the recombinant vaccine permits vaccination at an unexpectedly lower dosage than is normally used in similar vaccines in which the same protein is present in another recombinant virus. For example, immunization of mice with a single dose of as little as $10^4$ pfu of the recombinant, replication defective Ad containing a rabies glycoprotein has been observed to induce complete protection against rabies infection. Partial protection was seen seven days after immunization.

While not wishing to be bound by theory, the inventors currently believe that this recombinant, replication defective Ad vaccine is advantageous over, e.g., the vaccinia vaccine, because it permits lower doses of antigen to be expressed for an extended period of time by a non-lytic virus. For example, although vaccinia expresses higher doses of antigen, e.g., a rabies antigen, it is a lytic virus which causes a rapid demise of infected cells. The finding that the recombinant replication-defective Ad, e.g., Adrab.gp virus, used in the method of the present invention is more efficacious than the currently used vaccinia rabies (VRG) vaccine is unexpected and incompatible with current thinking that the antigenic dose governs the magnitude of the immune response. The use of the recombinant replication defective adenovirus also confers safety and efficacy advantages over other vaccine carriers, such as vaccinia. The adenovirus construct results in slow accumulation of the rabies virus G protein on the surface of infected cells without causing visible cell damage (data not shown). In contrast, cells infected with VRG recombinant rapidly express substantial amounts of the rabies virus G protein on the cell surface but then die shortly after infection. The adenoviral construct persists for at least seven days in immunocompetent mice.

With respect to safety, the present invention provides a recombinant replication-defective Ad which is thus highly unlikely to spread within a host or among individuals, particularly in view of the fact that the recombinant, E1-deleted dl7001 Ad virus, which is the backbone of the exemplary replication defective recombinant Ad used in the examples below has already been approved for use in humans for gene therapy, i.e., for the replacement of faulty or missing genes. The recombinant virus lacks oncogenic potential because the E1 gene that can function as an oncogene in some adenovirus strains has been deleted. Further, cells infected with the recombinant, replication defective adenovirus are completely eliminated by CD8 T cells within 21 days in immunocompetent hosts.

With respect to efficacy, the recombinant, replication defective Ad of this invention is highly efficacious at inducing cytolytic T cells and antibodies to the inserted heterologous protein expressed by the virus. This has been demonstrated with a recombinant, replication defective Ad containing a sequence encoding the rabies virus glycoprotein as the heterologous gene, which Ad has been administered to animals by other than the oral route.

The recombinant virus of this invention is also surprisingly more effective as a vaccine than other, previously reported, replication defective adenovirus vaccines. See, for example, Ragot et al, Eliot et al, and Jacobs et al, all cited above. In contrast to the other replication defective adenovirus vaccines, the vaccine composition useful in the present invention can be used at lower doses. This vaccine can also be administered in a single inoculation to obtain substantially complete protection.

For these reasons, the recombinant replication-defective adenovirus of the invention and particularly the preferred embodiment which makes use of the pAdCMV.lacZ (or H5.020CMVlacZ) Ad vector described below, can be used as a prophylactic or therapeutic vaccine against any pathogen for which the antigen(s) crucial for induction of an immune response able to limit the spread of the pathogen has been identified and for which the cDNA is available.

I. The Recombinant Adenovirus

As used herein, the term "minicassette" refers to the nucleotide sequence comprised of (a) a non-Ad promoter, which directs the replication and expression of (b) the following nucleotide sequence which encodes a heterologous protein immunogen, which is followed by (c) a polyA nucleotide sequence. By "vector or plasmid" is meant the construct comprised of 5' sequences of the Ad virus (usually Ad m.u. 0–1) deleted of the E1 gene (which occurs between Ad m.u. 1–9), which may contain a heterologous nucleotide sequence, but which does not contain the 3' end of the Ad virus (generally between about Ad m.u. 16 to 100), but rather conventional plasmid sequences. This vector does not contain all of the genes essential to a replicative virus. By "recombinant, replication defective Ad" is meant the infectious recombinant virus, deleted of its E1 gene, into which location is inserted the minicassette, and which contains all of the 3' sequences essential to an infectious virus except for a functional deletion in the E3 gene region.

The recombinant virus of the method of the invention is a replication-defective recombinant adenovirus containing a deletion of its E1 gene and at least a partial, functional deletion of its E3 gene. In the site of the E1 deletion a minicassette is inserted, which comprises a nucleotide sequence encoding a heterologous protein immunogen and a non-adenovirus promoter directing the replication and expression of the nucleotide sequence encoding the heterologous protein.

Any Ad that infects the target cells is appropriate for use in this invention. Desirable adenoviruses are human type C adenoviruses, including serotypes Ad2 and Ad5. The DNA sequences of a number of adenovirus types, including type Ad5, are available from GenBank [Accession No. M73260]. The adenovirus sequences may be obtained from any known adenovirus type, including the presently identified 41 human types [Horwitz et al, *Virology*, 2d ed., B. N. Fields, Raven Press, Ltd., New York (1990)]. Similarly, adenoviruses known to infect other animals may also be employed in this invention. The selection of the adenovirus type and strain is not anticipated to limit the following invention. A variety of adenovirus strains are available from the American Type Culture Collection, Rockville, Md., or available by request from a variety of commercial and institutional sources. In the following exemplary embodiment, an adenovirus type 5 (Ad5) sequence obtained from GenBank [Acc. No. M73260] is used for convenience.

Adenoviruses of the present invention are replication defective, i.e., intact adenoviruses which have been rendered replication defective by deleting the early gene locus that encodes E1a and E1b. See, K. F. Kozarsky and J. M. Wilson, *Curr. Opin. Genet. Dev.*, 3:499–503 (1993). Similarly, a replication defective adenovirus may be designed by deleting less than the entire E1a and E1b locus, but enough to functionally disable the E1 genes.

An additional characteristic of the Ad useful in this invention is that the E3 gene is deleted, i.e., from about m.u. 78.5 to about m.u. 84.3 of Ad5. While the presently preferred embodiment contains a complete deletion of that sequence, it may be possible to partially delete the E3 sequence to disable the functional abilities of the E3 gene.

A preferred recombinant Ad virus may be produced by using a plasmid vector pAd.CMVlacZ as described in FIG. 1B. This plasmid contains adenovirus sequences Ad m.u. 0–1 (i.e., it is fully deleted of E1a and E1b genes), after which a selected minigene may be inserted, e.g., the rabies glycoprotein under control of a heterologous promoter and other regulatory sequences, if desired, followed by the sequence Ad m.u.9 to 16 and plasmid sequences. When this vector is manipulated to place a minicassette into the E1 deletion site, and supplied with the remaining 3' Ad sequences with a full deletion of E3 and cultured in a helper cell line, the resulting recombinant adenovirus is capable of functioning as a rabies vaccine. This recombinant virus, called Adrab.gp or H5020.CMVrab, is described in detail in Example 1 and in flow chart form in FIGS. 1A through 1D.

The preferred recombinant Ad of this invention contains a minicassette which uses the cytomegalovirus (CMV) promoter [see, e.g., Boshart et al, *Cell,* 41:521–530 (1985)] to control the expression of the inserted heterologous gene. The promoter is inserted in the site of the E1 deletion and directs the replication and expression of the protein encoded by the selected heterologous gene. However, this invention is not limited by the selection of the promoter, except that the promoter should be heterologous to the Ad virus, i.e., the E1 Ad promoter is replaced using techniques known to those of skill in the art. Other desirable promoters include the Rous sarcoma virus LTR promoter/enhancer, the SV40 promoter, and the chicken cytoplasmic β-actin promoter [T. A. Kost et al, *Nucl. Acids Res.,* 11(23):8287 (1983)]. Still other promoter/enhancer sequences may be readily selected by one of skill in the art.

As discussed above, in the site of the E1 deletion, and under control of a promoter heterologous to Ad, a nucleic acid sequence, preferably in the form of DNA, encoding a protein heterologous to the Ad is inserted using techniques known to those of skill in the art.

The heterologous nucleic acid encodes a protein which is desirably capable of inducing an immune response to a pathogen. Such a protein may be a protein from rabies virus, human papilloma virus, human immunodeficiency virus (HIV), respiratory syncytial virus (RSV). The vaccine method of the present invention may also be employed with a tumor-associated protein specific for a selected malignancy. These tumor antigens include viral oncogenes, such as E6 and E7 of human papilloma virus or cellular oncogenes such as mutated ras or p53. Particularly, where the condition is human immunodeficiency virus (HIV) infection, the protein is preferably HIV glycoprotein 120 for which sequences are available from GenBank. Where the condition is human papilloma virus infection, the protein is selected from the group consisting of E6, E7 and/or L1 (Seedorf, K. et al, *Virol.,* 145:181–185 (1985)). Where the condition is respiratory syncytial virus infection, the protein is selected from the group consisting of the glyco—(G) protein and the fusion (F) protein, for which sequences are available from GenBank. In addition to these proteins, other virus-associated proteins are readily available to those of skill in the art. Selection of the heterologous proteins is not a limiting factor in this invention.

In a particularly preferred embodiment, the condition is rabies and the protein is the rabies glycoprotein [see, U.S. Pat. No. 4,393,201]. A variety of rabies strains are well known and available from academic and commercial sources, including depositaries such as the American Type Culture Collection, or may be isolated using known techniques. The strain used in the examples below is the Evelyn Rockitniki Abelseth (ERA) strain. However, this invention is not limited by the selection of the rabies strain.

In a preferred embodiment, cDNA encoding the rabies virus glycoprotein is inserted under control of a CMV promoter into the pAdCMV.lacZ (or H5.020CMVlacZ) Ad vector and supplied with the essential genes for infectivity and viral formation in a helper cell line using standard techniques, as described in detail in Example 1. Immunization studies revealed that a single administration of the resulting recombinant replciation defective virus conferred complete protection at a relatively low dose following challenge with rabies virus.

II. Formulation of Vaccine

A recombinant replication defective Ad bearing a gene encoding an immunogenic protein may be administered to a human or veterinary patient, preferably suspended in a biologically compatible solution or pharmaceutically acceptable delivery vehicle. A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccinal composition of the invention may be formulated to contain other components, including, e.g. adjuvants, stabilizers, pH adjusters, preservatives and the like. Such components are well known to those of skill in the vaccine art.

III. Administration of Vaccine

The recombinant, replication defective viruses are administered in an "effective amount", that is, an amount of recombinant virus that is effective in a route of administration to transfect the desired cells and provide sufficient levels of expression of the selected gene to provide a vaccinal benefit, i.e., protective immunity.

Conventional and pharmaceutically acceptable routes of administration include intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

Doses or effective amounts of the recombinant replication defective Ad virus will depend primarily on factors such as the condition, the selected gene, the age, weight and health of the animal, and may thus vary among animals. For example, a prophylactically effective amount or dose of the Ad vaccine is generally in the range of from about 100 $\mu$l to about 10 ml of saline solution containing concentrations of from about $1\times10^4$ to $1\times10^7$ plaque forming units (pfu) virus/ml. A preferred dose is from about 1 to about 10 ml saline solution at the above concentrations. The levels of immunity of the selected gene can be monitored to determine the need, if any, for boosters.

Currently, when vaccinating against rabies, the preferred dose is about $10^4$ pfu of the recombinant virus per mouse, preferably suspended in about 0.1 mL saline. Thus, when vaccinating against rabies infection, a larger animal would preferably be administered about a 1 mL dose containing about $1\times10^5$ Adrab.gp pfu suspended in saline. Following an assessment of antibody titers in the serum, optional booster immunizations may be desired.

The following examples illustrate the preferred methods for preparing the vectors and the recombinant viruses used in the vaccine and method of the invention. These examples are illustrative only and do not limit the scope of the invention.

EXAMPLE 1

Production and Purification of Vectors and Viruses

A. Adrab.gp

A recombinant, replication defective adenovirus expressing the rabies virus G protein of the Evelyn Rockitniki Abelseth (ERA) strain of rabies virus [ATCC VR-332; U.S. Pat. No. 3,423,505] (ERA) was constructed as follows. See the flowchart of FIGS. 1A to 1D.

The 1650 bp rabies virus G cDNA (nucleotides 1178 to 2827 of SEQ ID NO: 1) was purified from the pSG5rab.gp plasmid [S.R. Burger et al, *J. Gen. Virol.,* 72:359–367 (1991)] upon digestion with BglII, and blunt-ended with Klenow to supply the G gene. See also U.S. Pat. No. 4,393,201, issued Jul. 12, 1983.

The pAd.CMVlacZ vector [J. Wilson et al, *Hum. Gene Ther.,* 5:501–519 (1994); K. Kozarsky et al, *J. Biol. Chem.,* 269:13695–13702 (1994)], which contains Ad5 m.u. 0–1, followed by the cytomegalovirus (CMV) enhancer/promoter, the beta galactosidase (lacZ) gene, a polyadenylation signal (pA), adenovirus m.u. 9–16 and plasmid sequences from plasmid pAT153 including an origin of replication and ampicillin resistance gene, was completely digested with NotI to remove the lacZ gene and provide an ~5.6 kb backbone.

The cDNA encoding the rabies G protein, described above, was inserted into this 5.6 kb fragment via blunt-end cloning to generate pAdCMV.rabgp, which is similar to pAd.CMVlacZ but contains the rabies sequence in place of the lacZ gene. The appropriate orientation of the insert was confirmed by restriction enzyme mapping. pAdCMV.rabgp [SEQ ID NO: 1] contains adenovirus m.u. 0–1 (nucleotides 12 to 364 of SEQ ID NO: 1); followed by a cytomegalovirus enhancer/promoter (nucleotides 382 to 863 of SEQ ID NO: 1); the rabies glycoprotein gene (nucleotides 1178 to 2827 of SEQ ID NO: 1); a polyadenylation signal (nucleotides 2836–3034 of SEQ ID NO: 1); adenovirus m.u. 9–16 (nucleotides 3061 to 5524 of SEQ ID NO: 1); and plasmid sequences from plasmid pAT153 (nucleotides 5525 to 8236 of SEQ ID NO: 1). The remaining nucleotides of SEQ ID NO: 1 are the result of cloning and plasmid construction.

To provide a recombinant virus capable of infecting a cell, the 3' end of the adenovirus sequence was needed to replace the pAT153 plasmid sequences of pAdCMV.rabgp. The plasmid pAdCMV.rabgp was linearized with NheI. The linearized plasmid was co-transfected into 293 packaging cells [ATCC CRL 1573) which contain and express the transforming genes of human adenovirus type 5 to allow replication of the adenovirus (F. L. Graham et al, *J. Gen. Virol.,* 36:59–72 (1977)]. The transfected packaging cells were grown in DMEM with 10% FBS without HEPES buffer in a 5% $CO_2$ incubator with an E3 deleted Ad5 DNA [Ad5dl7001, a variant that carries a 3 kb deletion between m.u. 78.4 through 86 in the nonessential E3 region (provided by Dr. William Wold, Washington, University, St. Louis, Mo.)]. This Ad5dl7001 had been digested with a restriction enzyme ClaI to remove the left end, i.e., 917 bp from the 5' end of the adenovirus sequence, rendering the DNA non-infectious.

Following the co-transfection, only products of homologous recombination which occurred between Ad m.u. 9–16 of the pAdCMV.rabgp and the 5' deleted-Ad5dl7001 could produce replicative Ad virus in 293 cells. That is, when homologous recombination occurred, the 3' end of pAd.rabgp from about Ad m.u. 9 to about m.u. 16 and all of the plasmid sequence was swapped with the 3' end of the 5' truncated Ad5dl7001 virus, from about Ad m.u. 9 through m.u. 100.

Several recombinant viral plaques were harvested and tested for expression of the rabies virus G protein as described below. One recombinant, replication defective clone termed Adrab.gp was purified by two rounds of plaque purification and used for further studies and is illustrated schematically in FIG. 1D above.

The recombinant, replication defective Ad Adrab.gp contains Ad5 m.u. 0–1, followed by the CMV enhancer/promoter, the rabies G gene, a pA site, and Ad5 m.u. 9–78.4 and 86–100.

B. H5.010CMVlacZ

The recombinant replciation defective Ad, H5.010CMVlacZ, is substantially identical to Adrab.gp, except that this virus contains *E. coli* lacZ in place of the rabies G protein and only a partial deletion of E3.

The plasmid pAd.CMVlacZ described above, was linearized with NheI and co-transfected into 293 cells with a partially E3 deleted Ad5 DNA (sub 360 DNA, H5sub360), which had been digested with ClaI to eliminate the sequence of m.u. 83.5 to 85. As above, homologous recombination, followed by plaqing and harvesting produced the resulting recombinant adenovirus, designated H5.010CMVlacZ. This virus contains the sequence from Ad5 m.u. 0–1, followed by the CMV enhancer/promoter, the *Escherichia coli* lacZ gene, a pA site, and Ad5 m.u. 9–83.5 and 85–100.

C. Viral Propagation and Purification

The adenoviral recombinants, Adrab.gp H5.010CMVlacZ, and Ad5dl7001, a replication competent adenovirus, on 293 cells for 72 hours. Virus was recovered on the third round of freeze-thawing. Cell-free supernatants were either used directly or they were further purified by CsCl density centrifugation. Viral stocks were titrated on 293 cells using a plaque assay.

EXAMPLE 2

Immunofluorescence and T Cell Studies

To confirm that the Adrab.gp recombinant virus expresses the rabies virus G protein on infected cells in a form recognized by antibodies and cytolytic T cells directed against rabies virus, a series of in vitro experiments were performed initially.

A. Indirect Immunofluorescence

To assess the conformation of the G protein as expressed by the Adrab.gp virus, HeLa cells [which had been maintained in Dulbecco's minimal essential medium (DMEM) supplemented with 10% FBS, HEPES buffer and antibiotics in a 10% $CO_2$ incubator] were infected for 48 hours with 1 pfu of Adrab.gp virus per cell or as a control with H5.020CMVlacZ. Cells were stained 24 hours later by an indirect immunofluorescence assay using three MAbs (designated 523-11, 509-6, and 1112-1, and prepared using a 1:100 to 1:1000 dilution of ascitic fluid) to different conformation-dependent binding sites of the rabies virus G protein. The B cell hybridoma cells 509-6, 1112-1, and 523-11 secrete antibodies to different antigenic sites of the rabies virus G protein (509-6 to site I, 1112-1 to site II, and 523-11 to site III [T. J. Wiktor et al, *Proc. Natl. Acad. Sci. USA*, 75:3938–3945 (1978)]. These hybridoma cells were grown in DMEM supplemented with 10% FBS. Ascetic fluid was prepared in BALB/c mice. The assay was performed as follows.

The HeLa cells were infected for various times with 1 pfu of recombinant adenovirus or with 1 pfu of the vaccinia VRG virus described above per cell in 24-well Costar plates seeded with $5 \times 10^5$ cells per well. Cells were harvested at varied times after infection by treatment with trypsin and incubated for 60 minutes on ice with the MAbs identified above. Cells were washed once with phosphate-buffered saline (PBS) and then incubated with a FITC-labeled goat anti-mouse immunoglobulin (Ig) antibody. Cells were washed and analyzed by a fluorescence activated cell sorter (FACS). Alternatively cells adherent to glass cover slips were stained with the same antibody preparations for subsequent analysis with confocal microscopy.

For all of the antibodies, Adrab.gp virus-infected cells exhibited surface staining with the antibody, while cells infected with the control recombinant virus expressing lacZ were negative.

B. T Cell Proliferation Assay

Further in vitro studies showed that the recombinant virus Adrab.gp induced proliferation of a rabies virus G protein specific T helper cell clone in the presence of syngeneic, γ-irradiated splenocytes (FIG. 2). In a separate experiment, this T cell clone did not proliferate in the presence of H5.010CMVlacZ (data not shown).

A rabies virus-specific helper T cell clone, obtained from splenocytes of VRG immune C3H/He mice in the inventors' laboratory, was cultured ($2\times10^4$ cells/well) in 96-well round-bottom microtiter plate with $5\times10^5$ irradiated syngeneic C3H/He splenocytes pretreated with different antigen preparations (1, 0.1 and 0.01 pfu Adrab.gp per cell) in DMEM supplemented with 2% FBS and $10^{-6}$ M 2-mercaptoethanol and 10% rat Concanavalin A supernatant as a lymphokine source as described previously [L. Otvos, Jr., *Biochim. Biophys. Acta,* 1224:68–76 (1994)]. Proliferation of the cloned T cells was assessed 48 hours later by a 6 hour pulse with 0.5 $\mu$Ci of $^3$H-thymidine as described in H. C. J. Ertl et al, *Eur. J. Immunol.,* 21:1–10 (1991). Furthermore, mouse fibroblasts infected with the Adrab.gp recombinant virus were rendered susceptible to lysis by rabies virus G protein induced H-2 compatible cytolytic T cells.

Together these in vitro experiments demonstrated that Adrab.gp causes expression of the rabies virus G protein in a form that is readily recognized by both rabies virus-specific antibodies and T cells of the helper and the cytolytic subset. Specifically, FIG. 2 illustrates that Adrab.gp induces proliferation of a rabies virus G protein T helper cell clone in the presence of antigen presenting cells.

EXAMPLE 3

Immunization Studies

In the next set of experiments, mice were immunized with the Adrab.gp recombinant virus at several doses using different routes of immunization as follows. Groups of eight to twelve week old outbred ICR [Harlan Sprague-Dawley (Indianapolis, Ind.)] or C3H/He mice [The Jackson Laboratories (Bar Harbor, Me.)] were injected subcutaneously (s.c.), orally (per os), intranasally (i.n.), or upon anesthesia and surgical exposure of the trachea intratracheally (i.t.), with the recombinant adenoviruses of the previous examples diluted in 100 to 150 $\mu$l of saline. VRG [which had been propagated on HeLa cells as described in T. J. Wiktor et al, *Proc. Natl. Acad. Sci. USA,* 81:7194–7198 (1984)] was given s.c. Mice were bled by retro-orbital puncture in regular intervals after immunization to assess serum antibody titers.

The challenge virus standard (CVS)-24 strain of rabies virus, that is antigenically closely related to the ERA strain but shows higher virulence in mice, was derived from brain suspensions of infected newborn ICR mice [T. J. Wiktor et al, *J. Virol.*, 21:626–633 (1977]. Mice were challenged with 10 mean lethal doses ($LD_{50}$) of CVS-24 virus given intramuscularly (i.m.) into the masseter muscle; they were observed for the following 3 weeks for symptoms indicative of a rabies virus infection. Mice that developed complete bilateral hind leg paralysis (proceeding death by 24 to 48 hours) were euthanized for humanitarian reasons.

A. Virus Neutralizing Antibodies

Groups of ICR mice were immunized in three separate experiments with the different recombinant viruses given at the doses in Table 1 below either i.m., i.n., i.t., or per os. Mice inoculated into the trachea or i.n. were anesthetized prior to vaccination. Mice were bled 10 to 14 days later after a single immunization and serum antibody titers to rabies virus were tested by a neutralization assay. Virus neutralizing antibody (VNA) titers were determined on BHK-21 cells using infectious ERA virus at 1 pfu per cell [B. D. Dietzschold et al, *Virology*, 161:29–36 (1987)].

Table 1 below illustrates the data expressed as neutralization titers which are the reciprocal of the serum dilution resulting in a 50% reduction in the number of infected cells. Samples were assayed in duplicate in serial 3-fold dilutions starting with a dilution of 1:5. Standard deviations were within 10% for any given experiment.

As illustrated by the results in Table 1, virus given s.c., i.t., or i.n. induced a potent neutralizing antibody response if given at $10^6$ pfu. Oral immunization with Adrab.gp or systemic immunization with H5.020CMVlacZ failed to induce a measurable antibody response to rabies virus. The antibody responses to different doses of the recombinant replication-defective Adrab.gp were clearly superior to the response induced by the VRG recombinant. For example, the antibody titers of mice inoculated with as little as $2 \times 10^4$ pfu of Adrab.gp were more than 10 times higher than those of mice infected with $2 \times 10^6$ pfu of VRG (Table 1).

TABLE 1

Adrab.gp Recombinant Induces Neutralizing Antibodies to Rabies Virus

| Vaccine | Dose | Route of Immunizat'n | Time After | VNA titer Immunizat'n |
|---|---|---|---|---|
| Adrab.gp | $2 \times 10^6$ | s.c. | day 10 | 3,645 |
| Adrab.gp | $2 \times 10^5$ | s.c. | day 10 | 405 |
| Adrab.gp | $2 \times 10^4$ | s.c. | day 10 | 405 |
| VRG | $2 \times 10^6$ | s.c. | day 10 | 45 |
| VRG | $2 \times 10^5$ | s.c. | day 10 | 15 |
| VRG | $2 \times 10^4$ | s.c. | day 10 | 5 |
| None | — | — | day 10 | <5 |
| Adrab.gp | $10^4$ | s.c. | day 14 | 1,215 |
| Adrab.gp | $10^3$ | s.c. | day 14 | 405 |
| Adrab.gp | $10^2$ | s.c. | day 14 | <5 |
| Adrab.gp | $10^6$ | i.n. | day 14 | 1,215 |
| Adrab.gp | $10^6$ | i.t. | day 14 | 3,645 |
| Adrab.gp | $10^6$ | per os | day 14 | <5 |
| None | — | — | | <5 |

To ensure that the antibody response was caused by infection recombinant virus rather than by G protein fragments contaminating the virus-containing tissue culture supernatant used for immunization, mice were vaccinated with an equal dose of PFUs of unpurified and gradient purified recombinant adenovirus. Both groups of mice developed identical virus neutralizing antibody titers.

B. Cell-mediated Cytolysis

In addition to neutralizing antibodies, mice inoculated s.c. with Adrab.gp virus developed rabies virus G protein-specific cytolytic T cells able to kill H-2 compatible L929 target cells stably transfected with a plasmid vector expressing the rabies virus G protein under the control of the SV40 early promoter [Z. Q. Xiang et al, *J. Virol. Meth.*, 47:103–116 (1994)].

L929 mouse fibroblasts were maintained in Dulbecco's minimal essential medium (DMEM) supplemented with 10% fetal bovine serum (FBS), HEPES buffer and antibiotics in a 10% $CO_2$ incubator. L929 cells stably transfected with pSG5rab.gp [S.R. Burger et al, cited above], expressing the rabies virus G protein as well as L929 cells transfected with pSV2neo [ATCC Accession No. 37149) were maintained in 10% DMEM supplemented with 10% FBS. These cell lines used as target cells for cell-mediated cytolysis assays have been described in detail previously (Z. Q. Xiang et al, *J. Virol. Meth.*, 47:103–116 (1994)].

Briefly, splenocytes were harvested from immunized C3H/He mice. Single cells were prepared and incubated at $6 \times 10^6$ cells per well with 1 pfu per cell of the Adrab.gp recombinant virus in 1.6 ml of DMEM supplemented with $10^{-6}$ M 2-mercaptoethanol and 2% FBS for 5 days in a humidified 10% $CO_2$ incubator. The effector cells were then co-cultured with $^{51}$Cr-labeled L929 cells expressing the rabies virus G protein upon stable transfection with the pSG5rab.gp vector at varied effector-to-target cells ratios. To assess spontaneous release, $^{51}$Cr-labeled target cells were incubated with medium; to determine maximal release target cells were co-cultured with 10% sodium dodecyl sulfate. Cell-free supernatants were harvested 4 hours later and radioactivity was measured. Percentage of specific lysis was calculated by using the formula [Y. Yang et al, *Immunity*, 1:433–442 (1994)]:

$$100 \times [(\text{Release in presence of effectors} - \text{spontaneous release})/(\text{Maximal release} - \text{spontaneous release})]$$

Figure 3A:
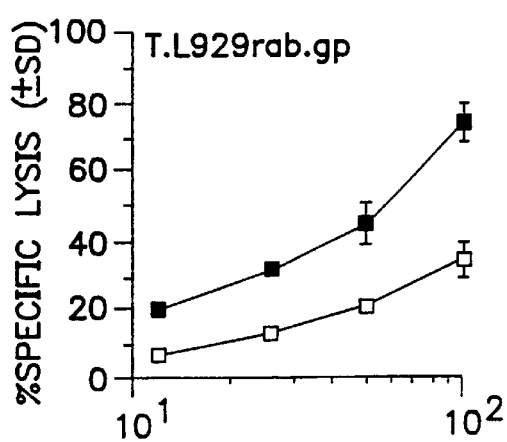
FIG. 3A is a graph plotting % specific lysis (means of triplicates±SD) vs. effector:target cell ratio for groups of C3H/He mice inoculated with $2 \times 10^6$ pfu of Adrab.gp (solid box) or H5.020CMVlacZ (open box), as described in Example 4B. Splenocytes were harvested 14 days later and co-cultured for 5 days with 1 pfu of Adrab.gp virus per cells. Activated lymphocytes were then tested at different E:T ratios on H-2 compatible L929 cells stably transfected with a rabies virus G protein-expressing vector (t.L929rab.gp) in a 4 hour $^{51}$Cr-release assay.
Figure 3B:
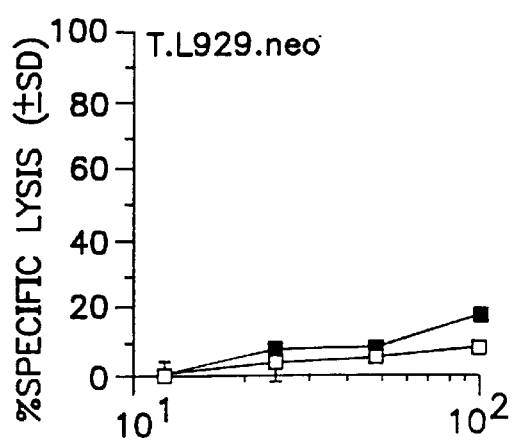
FIG. 3B is a graph of an experiment similar to FIG. 3A, but in which the activated lymphocytes were tested at different E:T ratios on H-2 compatible L929 cells stably transfected with a neomycin-expressing vector (t.L929.neo) in the $^{51}$Cr-release assay, as a control.
Figure 4A:
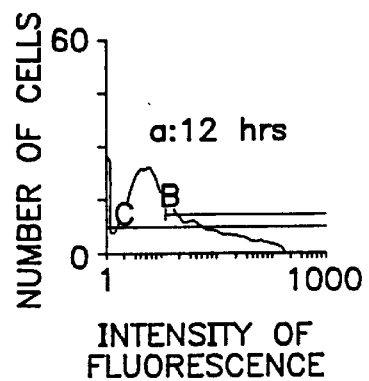
FIG. 4A is a graph plotting number of cells vs. intensity of fluorescence for L929 fibroblasts plated in 24-well Costar plates in medium supplemented with 2% fetal bovine serum (FBS) following infection with 1 pfu/cell of VRG, as described in Example 5 below. Cells harvested 12 hours after infection and stained by indirect immunofluorescence with monoclonal antibody (MAb) 509-6 were analyzed by fluorescence activated cell sorting (FACS). The line on the graph labeled "B" is the threshold below which 99% of the population are negative. Line "C" represents the region that encompasses all events on the histogram.
Figure 4B:
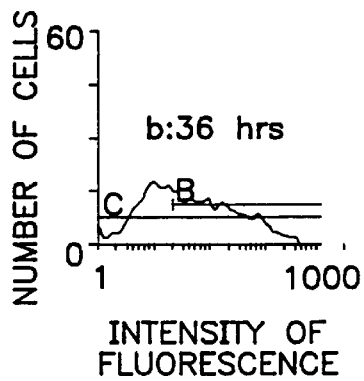
FIG. 4B is a graph similar to FIG. 4A above, except the cells were harvested 36 hours after infection.
Figure 4C:
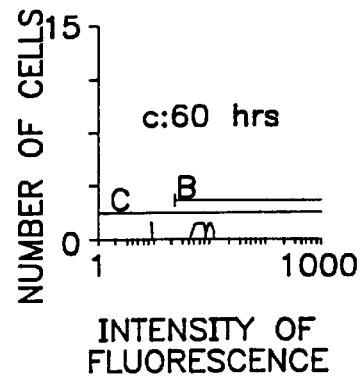
FIG. 4C is a graph similar to FIG. 4A above, except the cells were harvested 60 hours after infection.
Figure 4D:
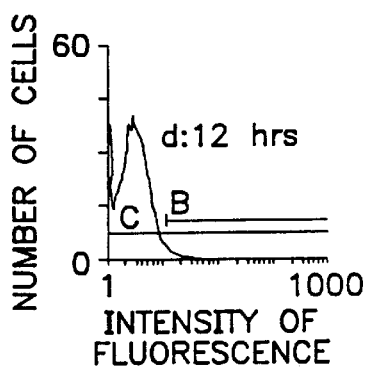
FIG. 4D is a graph similar to FIG. 4A above, except the cells, harvested 12 hours after infection, were stained using cells treated only with the fluorescein isothiocyanate (FITC)-labeled goat anti-mouse immunoglobulin (Ig) as a control.
Figure 4E:
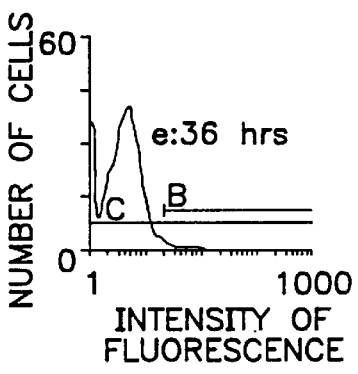
FIG. 4E is a graph similar to FIG. 4D above, except the cells were harvested 36 hours after infection.
Figure 4F:
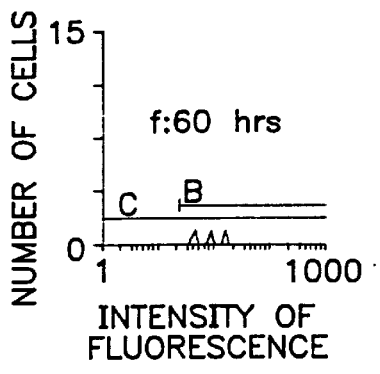
FIG. 4F is a graph similar to FIG. 4D above, except the cells were harvested 60 hours after infection.
Figure 4G:
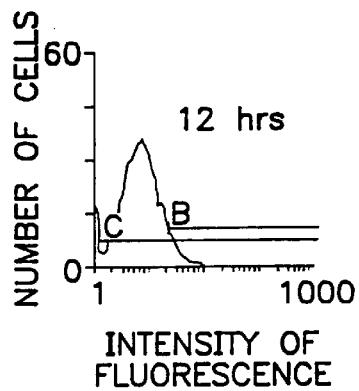
FIG. 4G is a graph similar to FIG. 4A above, except cells were infected with 1 pfu Adrab.gp virus, and cells were harvested 12 hours after infection.
Figure 4H:
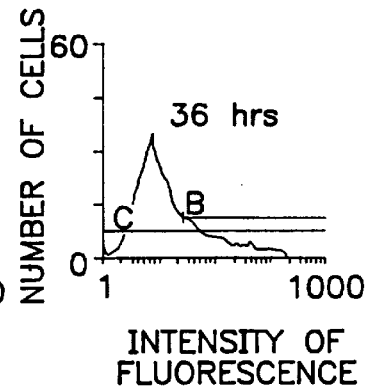
FIG. 4H is a graph similar to FIG. 4G, except the cells were harvested 36 hours after infection.
Figure 4I:
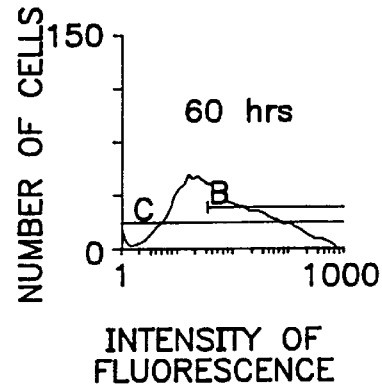
FIG. 4I is a graph similar to FIG. 4G, except the cells were harvested 60 hours after infection.
Figure 4J:
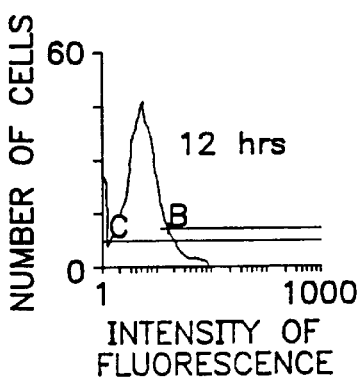
FIG. 4J is a graph similar to FIG. 4G above, except the cells were stained by indirect immunofluorescence using cells treated only with FITC-labeled goat anti-mouse Ig as a control.
Figure 4K:
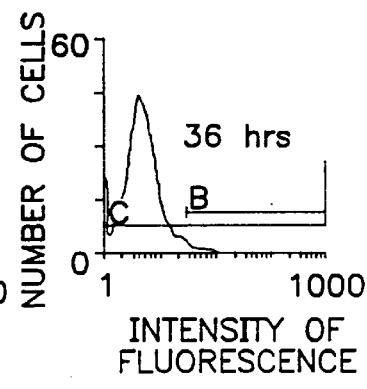
FIG. 4K is a graph similar to FIG. 4J above, except the cells were harvested 36 hours after infection.
Figure 4L:
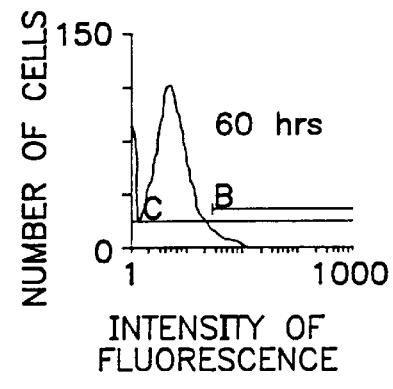
FIG. 4L is a graph similar to FIG. 4J above, except the cells were harvested 60 hours after infection.

The results are illustrated graphically in FIG. 3A, which illustrates that the Adrab.gp construct induces cytolytic T cells to the rabies virus G protein. See, also the results of FIG. 3B, in which lymphocytes were tested at different E:T ratios on an L929 cell line transfected with Adrab.gp or a neomycin expressing control.

EXAMPLE 4

Challenge Studies

Four different experiments were conducted in which mice, immunized as described in Example 3A above, were challenged with 10 $LD_{50}$ of rabies virus. Briefly, mice immunized with the Adrab.gp or the VRG recombinant virus were challenged 2 to 5 weeks after immunization with 10 $LD_{50}$ of the virulent CVS-24 strain of rabies virus given i.m. into the masseter muscle. Mice that subsequently developed complete bilateral hind leg paralysis indicative of a terminal rabies virus infection were euthanized for humanitarian reasons. Survivors were observed for a total of 21 days.

The results are illustrated in Table 2 below. Mice immunized with Adrab.gp i.m., i.t., or i.n. using doses ranging from $10^4$ to $2 \times 10^6$ pfu were fully protected against infection; 87% of mice inoculated with $10^3$ pfu were protected. All mice immunized with only $10^2$ pfu of the recombinant adenovirus or inoculated with the H5.020CMVlacZ control virus ($2 \times 10^6$ pfu) or with Adrab.gp per os developed a fatal rabies virus encephalitis within 10 days after infection. Mice vaccinated with VRG showed partial protection; the group receiving the highest dose, i.e., $2 \times 10^6$ pfu, had a mortality rate above 50% raising to ~90% in mice inoculated with $2 \times 10^4$ pfu of VRG.

TABLE 2

Adrab.gp Recombinant Virus Induces Protective Immunity to Challenge with Rabies Virus

| Vaccine | Dose | Route of immunization | % mortality |
|---|---|---|---|
| Adrab.gp | $2 \times 10^6$ | s.c. | 0 |
| H5.010CNVlacZ | $2 \times 10^6$ | s.c. | 90 |
| Adrab.gp | $2 \times 10^6$ | s.c. | 0 |
| Adrab.gp | $2 \times 10^5$ | s.c. | 0 |
| Adrab.gp | $2 \times 10^4$ | s.c. | 0 |
| VRG | $2 \times 10^6$ | s.c. | 56 |
| VRG | $2 \times 10^5$ | s.c. | 71 |
| VRG | $2 \times 10^4$ | s.c. | 86 |
| None | — | — | 100 |
| Adrab.gp | $10^4$ | s.c. | 0 |
| Adrab.gp | $10^3$ | s.c. | 13 |
| Adrab.gp | $10^2$ | s.c. | 100 |
| None | — | — | 100 |
| Adrab.gp | $10^6$ | i.n. | 0 |
| Adrab.gp | $10^6$ | i.t. | 0 |
| Adrab.gp | $10^6$ | per os | 100 |
| None | — | — | 100 |

EXAMPLE 5

Comparison Studies

The relationship between the magnitude of an immune response and the amount of antigen available to induce naive T and B cells was studied. As determined by immunofluorescence and subsequent analysis by FACS (FIGS. 4A–4L), both the VRG and the Adrab.gp recombinants express comparable levels of the rabies virus G protein but the kinetics of expression are different. Cells infected with the VRG virus express high levels of G protein within 12 hours after infection; these levels increased over the next day. By 60 hours the VRG virus has completely lysed a cell population infected with ~1 pfu of virus per cell.

The same cell line infected with 1 pfu of Adrab.gp per cell shows low expression of the rabies virus G protein on day 1. The level of expression increases until days 3 to 4 after infection and then reaches plateau levels (data shown for days 1 to 3 in FIG. 4A through FIG. 4L). The replication-defective recombinant adenoviruses are non-lytic and maintain stable infection and expression of virus-encoded proteins for extended periods of time. In tissue culture, expression has been shown for 7 days in vivo; using the H5.010CMVlacZ recombinant virus, stable levels of expression were demonstrated in immunocompromised mice for 10 months.

A non-lytic virus, e.g., the recombinant replication defective adenovirus, that expresses antigens for prolonged periods of time might thus be more immunogenic compared to a replicating agent that causes death of the infected cells within 24 to 48 hours, e.g., vaccinia.

Figure 5A:
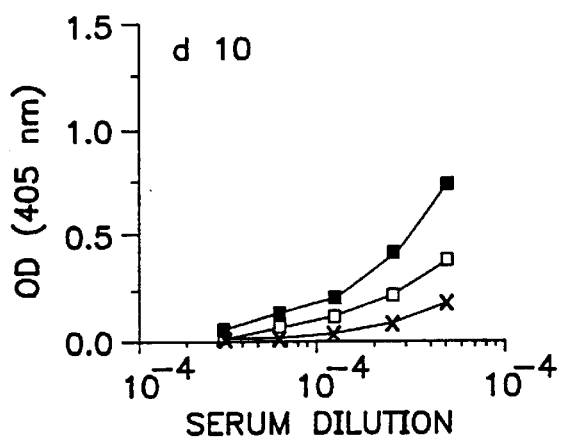
FIG. 5A is a graph plotting optical density at 405 nm vs. serum dilution for duplicate samples±SD, as described in Example 6B below for mice immunized with a replication-competent E3 deleted adenovirus (open box) or Adrab.gp (solid box). Native age-matched control mice were used as controls (X). Mice were bled 10 days after immunization and serum antibody titers to adenoviral antigens were determined by an ELISA on plates coated with 1 μg/mL of purified H5.020CMVlacZ virus.
Figure 5B:
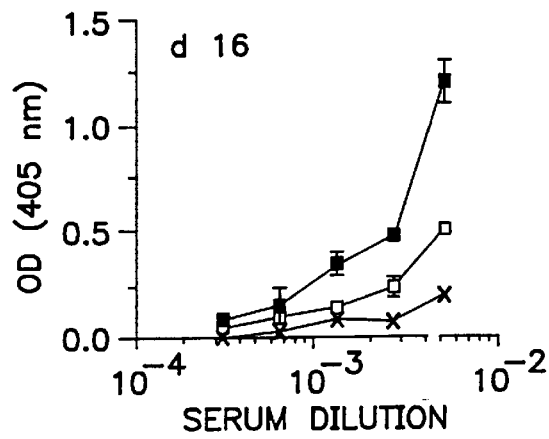
FIG. 5B is a graph similar to that of FIG. 5A for mice immunized as described in FIG. 6A below, and bled at 16 days.

To substantiate this hypothesis, the inventors compared the immune response to rabies proteins upon immunization of mice with a replication-defective E1 deleted adenovirus and a replication-competent adenovirus. Both adenoviruses were of the human strain 5 and both were deleted in E3. These recombinant viruses were tested by enzyme linked immunoadsorbent assay (ELISA) (FIGS. 5A and 5B). The ELISAs were conducted in 96-well microtiter plates coated with 0.1 to 0.2 µg per well of ERA-BPL virus or 1–2 µg per well of purified H5.010CMVlacZ virus, using an alkaline phosphatase conjugated goat anti-mouse Ig as second antibody as described in detail in Xiang and Ertl, *Virus Res.*, 24:297–314 (1992). As shown in FIGS. 5A and 5B, the antibody response to the E1 deleted Adrab.gp virus (solid box) was superior to that of a replication competent Ad virus (open box). This supports the position that long-term expression of viral antigens by a non-lytic virus can induce stronger immune response compared to short-term expression by a replication-competent agent. FIGS. 5A and 5B illustrate that expression of E1 causes a reduction in the antibody response to adenovirus.

These studies demonstrate that the recombinant replication-defective adenovirus used in the present invention shows higher immunogenicity compared to a replication-competent adenovirus. Without wishing to be bound by theory, it is believed that the length of expression of the antigen plays a role in induction of the immune response. In similar studies comparing the replication defective adenovirus vaccine to the VRG vaccine, the Ad vaccine expresses the rabies antigen longer than the VRG recombinant virus vaccine.

EXAMPLE 6

Further Comparative Studies

The following study was performed to test if pre-existing immunity to adenoviral proteins interferes with stimulation of a rabies G protein-specific immune response to the Adrab.gp construct. Groups of C3H/He mice were immunized with $10^5$ or $10^6$ pfu of a replication-competent adenovirus human serotype 5 that had been deleted of the E3 gene. Mice were injected 4 weeks later with $10^6$ pfu of Adrab.gp. Control mice were only injected with Adrab.gp ($10^6$ pfu). Mice were bled 12 days later and neutralizing antibody titers were determined (Table 3).

TABLE 3

The Effect of Pre-Existing Immunity to Adenovirus on the Rabies VNA Response to the Adrab.gp Vaccine

| Pre-immunization Titer | Immunization | VNA |
|---|---|---|
| None | $10^6$ pfu Adrab.gp | 3.645 |
| $10^5$ pfu Ad5d17001 | $10^6$ pfu Adrab.gp | 3.645 |
| $10^6$ pfu Ad517001 | $10^6$ pfu Adrab.gp | 1.215 |
| None | None | <5 |

Mice pre-immunized with adenovirus developed VNA to rabies virus upon booster immunization with the Adrab.gp construct. Titers were equivalent, or marginally lower, when compared to those in control mice that had only received Adrab.gp, indicating that antibodies to adenoviruses only marginally inhibit the B cell response to proteins expressed by adenovirus recombinants. When tested in comparison to a reference serum provided by the World Health Organization, sera from pre-immune (both doses of adenovirus) or naive mice were shown to have titers of 40 IU to rabies virus. Protection to rabies virus is correlated to antibody titers and 2 IU are considered sufficient to protect against a severe challenge. Pre-immunity to adenovirus does, thus, not impair the ability of the Adrab.gp vaccine to elicit protective immunity.

Figure 6A:
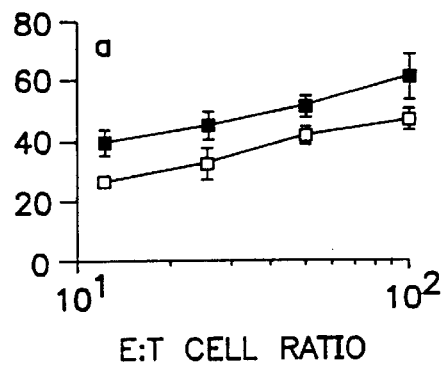
FIG. 6A is a graph plotting mean percentage (%) specific lysis of triplicates±SD vs. E:T cell ratio for C3H/He mice inoculated with $10^6$ pfu of replication competent E3 deleted adenovirus and boosted 3 weeks later with Adrab.gp (open box). Control mice were inoculated with Adrab.gp only (solid box). Mice were sacrificed 4 weeks later and upon restimulation with 1 pfu of Adrab.gp per cell tested on a 4 hour $^{51}$Cr-release assay on L929 cells stably transfected with pSG5rab.gp. See Example 6.
Figure 6B:
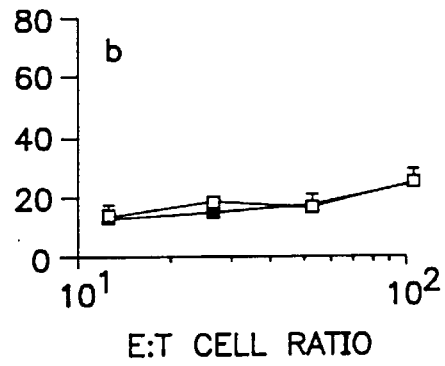
FIG. 6B is a graph similar to FIG. 6A, except the L929 cells were transfected with pSV2neo.

Similar data were obtained for the stimulation of cytolytic T cells to rabies virus-infected cells, pre-immune animals showed somewhat lower lysis compared to the control group (see FIGS. 6A and 6B). FIGS. 6A and 6B illustrate that the cytolytic T cell response to rabies virus G protein expressing target cells upon immunization with Adrab.gp is only slightly reduced in animals immune to adenovirus. Nevertheless, adenovirus-immune mice still developed significant T cell responses to the rabies virus G protein upon immunization with Adrab.gp.

EXAMPLE 7

Additional Challenge Studies

In this experiment the kinetic of the induction of protective immunity upon vaccination was tested with the Adrab.gp virus. Vaccination to rabies virus is in general given post-exposure, hence it is crucial for the vaccine to induce a rapid immune response before the rabies virus has reached the central nervous system.

Figure 7:
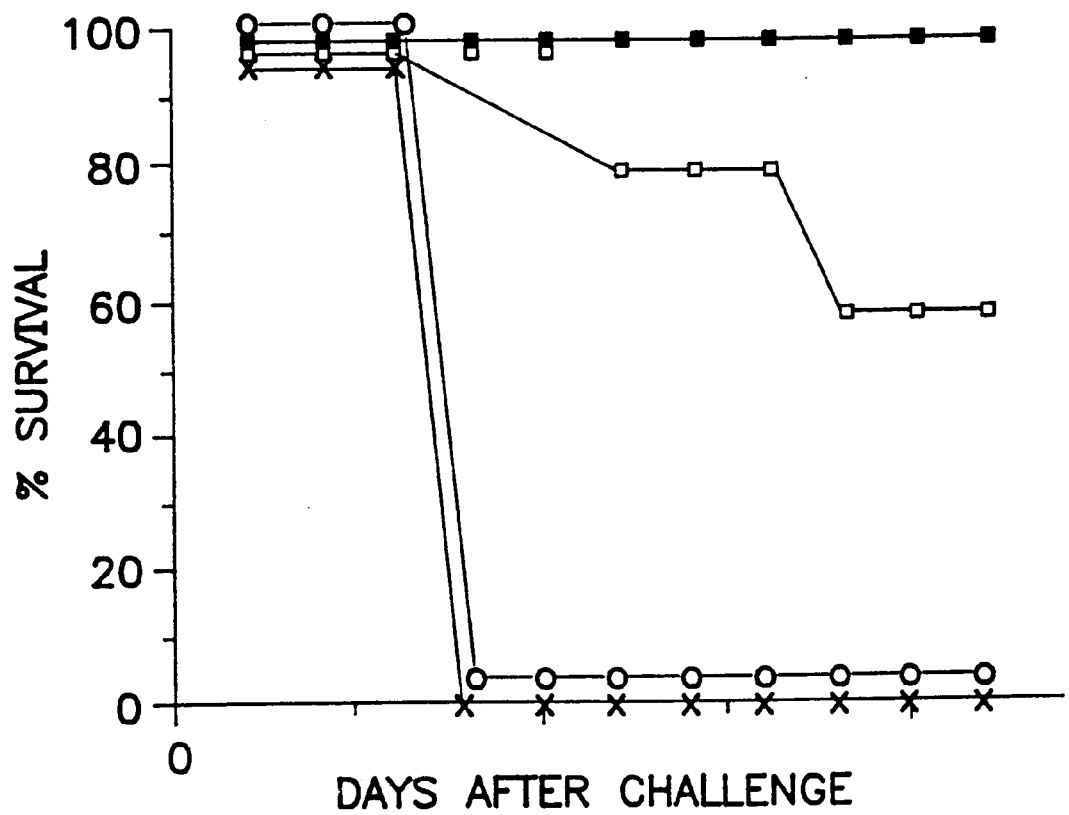
FIG. 7 is a graph plotting % survival of vaccinated mice vs. days after challenge with rabies virus. Mice were challenged 3 days (open triangle), 7 days (open square), and 10 days (solid square) after vaccination. X represents naive mice controls. See, Example 7.

Mice were immunized with 10 PFU of Adrab.gp s.c. Immunized mice were challenged 3 (◊), 7 (□), and 10 (■) days after vaccination with 10 $LD_{50}$ of rabies virus given i.m. Naive mice (X) served as controls. Mice were observed for four weeks to record mortality. As shown in FIG. 7, mice vaccinated with Adrab.gp virus 10 days previously were completely protected; while more than half of the animals were protected as early as seven days after a single injection. Mice vaccinated three days before challenge succumbed to the infection.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method of inducing an immune response against human papilloma virus comprising: administering to a mammalian subject a sufficient amount of a recombinant adenovirus comprising a human serotype 5 adenovirus containing a complete deletion of its E1 gene and at least a functional deletion of its E3 gene, and, in the site of the E1 gene deletion, a sequence comprising a cytomegalovirus promoter directing the replication and expression of DNA encoding a human papilloma virus protein, which when administered to the subject in said recombinant virus, elicits a protective immune response against human papilloma virus.

2. The method according to claim 1 wherein said heterologous protein is HPV-E6.

3. The method according to claim 1 wherein said heterologous protein is HPV-E7.

4. The method according to claim 1 wherein said heterologous protein is HPV-L1.

5. The method according to claim 1 wherein said sufficient amount comprises a single dose of said recombinant adenovirus.

6. The method according to claim 5 wherein a single dose of about $10^7$ pfu of said adenovirus is administered to the subject.

* * * * *

```
                        SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
             (A) LENGTH: 8236 base pairs
             (B) TYPE: nucleic acid
             (C) STRANDEDNESS: double
             (D) TOPOLOGY: Not Relevant (ii) MOLECULE TYPE: cDNA (ix) FEATURE:
             (A) NAME/KEY: CDS
             (B) LOCATION: 1185..2756

(xi) SEQUENCE DESCRIPTION: SEQ ID NO:1:

GAATTCGCTA GCATCATCAA TAATATACCT TATTTTGGAT TGAAGCCAAT             50

ATGATAATGA GGGGGTGGAG TTTGTGACGT GGCGCGGGGC GTGGGAACGG            100

GGCGGGTGAC GTAGTAGTGT GGCGGAAGTG TGATGTTGCA AGTGTGGCGG            150

AACACATGTA AGCGACGGAT GTGGCAAAAG TGACGTTTTT GGTGTGCGCC            200

GGTGTACACA GGAAGTGACA ATTTTCGCGC GGTTTTAGGC GGATGTTGTA            250

GTAAATTTGG GCGTAACCGA GTAAGATTTG GCCATTTTCG CGGGAAAACT            300

GAATAAGAGG AAGTGAAATC TGAATAATTT TGTGTTACTC ATAGCGCGTA            350

ATATTTGTCT AGGGAGATCA GCCTGCAGGT CGTTACATAA CTTACGGTAA            400

ATGGCCCGCC TGGCTGACCG CCCAACGACC CCCGCCCATT GACGTCAATA            450

ATGACGTATG TTCCCATAGT AACGCCAATA GGGACTTTCC ATTGACGTCA            500

ATGGGTGGAG TATTTACGGT AAACTGCCCA CTTGGCAGTA CATCAAGTGT            550

ATCATATGCC AAGTACGCCC CCTATTGACG TCAATGACGG TAAATGGCCC            600

GCCTGGCATT ATGCCCAGTA CATGACCTTA TGGGACTTTC CTACTTGGCA            650

GTACATCTAC GTATTAGTCA TCGCTATTAC CATGGTGATG CGGTTTTGGC            700

AGTACATCAA TGGGCGTGGA TAGCGGTTTG ACTCACGGGG ATTTCCAAGT            750

CTCCACCCCA TTGACGTCAA TGGGAGTTTG TTTTGGCACC AAAATCAACG            800
```

-continued

```
GGACTTTCCA AAATGTCGTA ACAACTCCGC CCCATTGACG CAAATGGGCG                                 850

GTAGGCGTGT ACGGTGGGAG GTCTATATAA GCAGAGCTCG TTTAGTGAAC                                 900

CGTCAGATCG CCTGGAGACG CCATCCACGC TGTTTTGACC TCCATAGAAG                                 950

ACACCGGGAC CGATCCAGCC TCCGGACTCT AGAGGATCCG GTACTCGAGG                                1000

AACTGAAAAA CCAGAAAGTT AACTGGTAAG TTTAGTCTTT TTGTCTTTTA                                1050

TTTCAGGTCC CGGATCCGGT GGTGGTGCAA ATCAAAGAAC TGCTCCTCAG                                1100

TGGATGTTGC CTTTACTTCT AGGCCTGTAC GGAAGTGTTA CTTCTGCTCT                                1150

AAAAGCTGCG GAATTGTACC CGCGGCCAGG AAAG ATG GTT CCT CAG                                1196
                                      Met Val Pro Gln
                                        1

GCT CTC CTG TTT GTA CCC CTT CTG GTT TTT CCA TTG TGT TTT                               1238
Ala Leu Leu Phe Val Pro Leu Leu Val Phe Pro Leu Cys Phe
 5              10              15

GGG AAA TTC CCT ATT TAC ACG ATA CTA GAC AAG CTT GGT CCC                               1280
Gly Lys Phe Pro Ile Tyr Thr Ile Leu Asp Lys Leu Gly Pro
    20              25              30

TGG AGC CCG ATT GAC ATA CAT CAC CTC AGC TGC CCA AAC AAT                               1322
Trp Ser Pro Ile Asp Ile His His Leu Ser Cys Pro Asn Asn
        35              40              45

TTG GTA GTG GAG GAC GAA GGA TGC ACC AAC CTG TCA GGG TTC                               1364
Leu Val Val Glu Asp Glu Gly Cys Thr Asn Leu Ser Gly Phe
            50              55              60

TCC TAC ATG GAA CTT AAA GTT GGA TAC ATC TTA GCC ATA AAA                               1406
Ser Tyr Met Glu Leu Lys Val Gly Tyr Ile Leu Ala Ile Lys
                65              70

ATG AAC GGG TTC ACT TGC ACA GGC GTT GTG ACG GAG GCT GAA                               1448
Met Asn Gly Phe Thr Cys Thr Gly Val Val Thr Glu Ala Glu
 75              80              85

ACC TAC ACT AAC TTC GTT GGT TAT GTC ACA ACC ACG TTC AAA                               1490
Thr Tyr Thr Asn Phe Val Gly Tyr Val Thr Thr Thr Phe Lys
    90              95              100

AGA AAG CAT TTC CGC CCA ACA CCA GAT GCA TGT AGA GCC GCG                               1532
Arg Lys His Phe Arg Pro Thr Pro Asp Ala Cys Arg Ala Ala
        105             110             115

TAC AAC TGG AAG ATG GCC GGT GAC CCC AGA TAT GAA GAG TCT                               1574
Tyr Asn Trp Lys Met Ala Gly Asp Pro Arg Tyr Glu Glu Ser
            120             125             130

CTA CAC AAT CCG TAC CCT GAC TAC CGC TGG CTT CGA ACT GTA                               1616
Leu His Asn Pro Tyr Pro Asp Tyr Arg Trp Leu Arg Thr Val
                135             140

AAA ACC ACC AAG GAG TCT CTC GTT ATC ATA TCT CCA AGT GTA                               1658
Lys Thr Thr Lys Glu Ser Leu Val Ile Ile Ser Pro Ser Val
145             150             155

GCA GAT TTG GAC CCA TAT GAC AGA TCC CTT CAC TCG AGG GTC                               1700
Ala Asp Leu Asp Pro Tyr Asp Arg Ser Leu His Ser Arg Val
    160             165             170

TTC CCT AGC GGG AAG TGC TCA GGA GTA GCG GTG TCT TCT ACC                               1742
Phe Pro Ser Gly Lys Cys Ser Gly Val Ala Val Ser Ser Thr
        175             180             185

TAC TGC TCC ACT AAC CAC GAT TAC ACC ATT TGG ATG CCC GAG                               1784
Tyr Cys Ser Thr Asn His Asp Tyr Thr Ile Trp Met Pro Glu
            190             195             200

AAT CCG AGA CTA GGG ATG TCT TGT GAC ATT TTT ACC AAT AGT                               1826
Asn Pro Arg Leu Gly Met Ser Cys Asp Ile Phe Thr Asn Ser
                205             210

AGA GGG AAG AGA GCA TCC AAA GGG AGT GAG ACT TGC GGC TTT                               1868
```

-continued

```
Arg Gly Lys Arg Ala Ser Lys Gly Ser Glu Thr Cys Gly Phe
215                 220                 225

GTA GAT GAA AGA GGC CTA TAT AAG TCT TTA AAA GGA GCA TGC          1910
Val Asp Glu Arg Gly Leu Tyr Lys Ser Leu Lys Gly Ala Cys
    230                 235                 240

AAA CTC AAG TTA TGT GGA GTT CTA GGA CTT AGA CTT ATG GAT          1952
Lys Leu Lys Leu Cys Gly Val Leu Gly Leu Arg Leu Met Asp
                245                 250                 255

GGA ACA TGG GTC GCG ATG CAA ACA TCA AAT GAA ACC AAA TGG          1994
Gly Thr Trp Val Ala Met Gln Thr Ser Asn Glu Thr Lys Trp
            260                 265                 270

TGC CCT CCC GAT CAG TTG GTG AAC CTG CAC GAC TTT CGC TCA          2036
Cys Pro Pro Asp Gln Leu Val Asn Leu His Asp Phe Arg Ser
                275                 280

GAC GAA ATT GAG CAC CTT GTT GTA GAG GAG TTG GTC AGG AAG          2078
Asp Glu Ile Glu His Leu Val Val Glu Glu Leu Val Arg Lys
285                 290                 295

AGA GAG GAG TGT CTG GAT GCA CTA GAG TCC ATC ATG ACA ACC          2120
Arg Glu Glu Cys Leu Asp Ala Leu Glu Ser Ile Met Thr Thr
    300                 305                 310

AAG TCA GTG AGT TTC AGA CGT CTC AGT CAT TTA AGA AAA CTT          2162
Lys Ser Val Ser Phe Arg Arg Leu Ser His Leu Arg Lys Leu
                315                 320                 325

GTC CCT GGG TTT GGA AAA GCA TAT ACC ATA TTC AAC AAG ACC          2204
Val Pro Gly Phe Gly Lys Ala Tyr Thr Ile Phe Asn Lys Thr
                330                 335                 340

TTG ATG GAA GCC GAT GCT CAC TAC AAG TCA GTC AGA ACT TGG          2246
Leu Met Glu Ala Asp Ala His Tyr Lys Ser Val Arg Thr Trp
                345                 350

AAT GAG ATC CTC CCT TCA AAA GGG TGT TTA AGA GTT GGG GGG          2288
Asn Glu Ile Leu Pro Ser Lys Gly Cys Leu Arg Val Gly Gly
355                 360                 365

AGG TGT CAT CCT CAT GTG AAC GGG GTG TTT TTC AAT GGT ATA          2330
Arg Cys His Pro His Val Asn Gly Val Phe Phe Asn Gly Ile
    370                 375                 380

ATA TTA GGA CCT GAC GGC AAT GTC TTA ATC CCA GAG ATG CAA          2372
Ile Leu Gly Pro Asp Gly Asn Val Leu Ile Pro Glu Met Gln
                385                 390                 395

TCA TCC CTC CTC CAG CAA CAT ATG GAG TTG TTG GAA TCC TCG          2414
Ser Ser Leu Leu Gln Gln His Met Glu Leu Leu Glu Ser Ser
                400                 405                 410

GTT ATC CCC CTT GTG CAC CCC CTG GCA GAC CCG TCT ACC GTT          2456
Val Ile Pro Leu Val His Pro Leu Ala Asp Pro Ser Thr Val
                415                 420

TTC AAG GAC GGT GAC GAG GCT GAG GAT TTT GTT GAA GTT CAC          2498
Phe Lys Asp Gly Asp Glu Ala Glu Asp Phe Val Glu Val His
425                 430                 435

CTT CCC GAT GTG CAC AAT CAG GTC TCA GGA GTT GAC TTG GGT          2540
Leu Pro Asp Val His Asn Gln Val Ser Gly Val Asp Leu Gly
    440                 445                 450

CTC CCG AAC TGG GGG AAG TAT GTA TTA CTG AGT GCA GGG GCC          2582
Leu Pro Asn Trp Gly Lys Tyr Val Leu Leu Ser Ala Gly Ala
                455                 460                 465

CTG ACT GCC TTG ATG TTG ATA ATT TTC CTG ATG ACA TGT TGT          2624
Leu Thr Ala Leu Met Leu Ile Ile Phe Leu Met Thr Cys Cys
                470                 475                 480

AGA AGA GTC AAT CGA TCA GAA CCT ACG CAA CAC AAT CTC AGA          2666
Arg Arg Val Asn Arg Ser Glu Pro Thr Gln His Asn Leu Arg
                485                 490
```

-continued

| | |
|---|---|
| GGG ACA GGG AGG GAG GTG TCA GTC ACT CCC CAA AGC GGG AAG<br>Gly Thr Gly Arg Glu Val Ser Val Thr Pro Gln Ser Gly Lys<br>495                 500                              505 | 2708 |
| ATC ATA TCT TCA TGG GAA TCA CAC AAG AGT GGG GGT GAG ACC<br>Ile Ile Ser Ser Trp Glu Ser His Lys Ser Gly Gly Glu Thr<br>    510                        515                       520 | 2750 |
| AGA CTG TGAGGACTGG CCGTCCTTTC AACGATCCAA GTCCTGAAGA<br>Arg Leu | 2796 |
| TCACCTCCCC TTGGGGGGTT CTTTTTAAAA AGGCCGCGGG GATCCAGACA | 2846 |
| TGATAAGATA CATTGATGAG TTTGGACAAA CCACAACTAG AATGCAGTGA | 2896 |
| AAAAAATGCT TTATTTGTGA AATTTGTGAT GCTATTGCTT TATTTGTAAC | 2946 |
| CATTATAAGC TGCAATAAAC AAGTTAACAA CAACAATTGC ATTCATTTTA | 2996 |
| TGTTTCAGGT TCAGGGGGAG GTGTGGGAGG TTTTTTCGGA TCCTCTAGAG | 3046 |
| TCGACCTGCA GGCTGATCTG GAAGGTGCTG AGGTACGATG AGACCCGCAC | 3096 |
| CAGGTGCAGA CCCTGCGAGT GTGGCGGTAA ACATATTAGG AACCAGCCTG | 3146 |
| TGATGCTGGA TGTGACCGAG GAGCTGAGGC CCGATCACTT GGTGCTGGCC | 3196 |
| TGCACCCGCG CTGAGTTTGG CTCTAGCGAT GAAGATACAG ATTGAGGTAC | 3246 |
| TGAAATGTGT GGGCGTGGCT TAAGGGTGGG AAAGAATATA TAAGGTGGGG | 3296 |
| GTCTTATGTA GTTTTGTATC TGTTTTGCAG CAGCCGCCGC CGCCATGAGC | 3346 |
| ACCAACTCGT TGATGGAAG CATTGTGAGC TCATATTTGA CAACGCGCAT | 3396 |
| GCCCCCATGG GCCGGGGTGC GTCAGAATGT GATGGGCTCC AGCATTGATG | 3446 |
| GTCGCCCCGT CCTGCCCGCA AACTCTACTA CCTTGACCTA CGAGACCGTG | 3496 |
| TCTGGAACGC CGTTGGAGAC TGCAGCCTCC GCCGCCGCTT CAGCCGCTGC | 3546 |
| AGCCACCGCC CGCGGGATTG TGACTGACTT TGCTTTCCTG AGCCCGCTTG | 3596 |
| CAAGCAGTGC AGCTTCCCGT TCATCCGCCC GCGATGACAA GTTGACGGCT | 3646 |
| CTTTTGGCAC AATTGGATTC TTTGACCCGG GAACTTAATG TCGTTTCTCA | 3696 |
| GCAGCTGTTG GATCTGCGCC AGCAGGTTTC TGCCCTGAAG GCTTCCTCCC | 3746 |
| CTCCCAATGC GGTTTAAAAC ATAAATAAAA AACCAGACTC TGTTTGGATT | 3796 |
| TGGATCAAGC AAGTGTCTTG CTGTCTTTAT TTAGGGGTTT TGCGCGCGCG | 3846 |
| GTAGGCCCGG GACCAGCGGT CTCGGTCGTT GAGGGTCCTG TGTATTTTTT | 3896 |
| CCAGGACGTG GTAAAGGTGA CTCTGGATGT TCAGATACAT GGGCATAAGC | 3946 |
| CCGTCTCTGG GGTGGAGGTA GCACCACTGC AGAGCTTCAT GCTGCGGGGT | 3996 |
| GGTGTTGTAG ATGATCCAGT CGTAGCAGGA GCGCTGGGCG TGGTGCCTAA | 4046 |
| AAATGTCTTT CAGTAGCAAG CTGATTGCCA GGGGCAGGCC CTTGGTGTAA | 4096 |
| GTGTTTACAA AGCGGTTAAG CTGGGATGGG TGCATACGTG GGGATATGAG | 4146 |
| ATGCATCTTG GACTGTATTT TTAGGTTGGC TATGTTCCCA GCCATATCCC | 4196 |
| TCCGGGGATT CATGTTGTGC AGAACCACCA GCACAGTGTA TCCGGTGCAC | 4246 |
| TTGGGAAATT TGTCATGTAG CTTAGAAGGA AATGCGTGGA AGAACTTGGA | 4296 |
| GACGCCCTTG TGACCTCCAA GATTTTCCAT GCATTCGTCC ATAATGATGG | 4346 |
| CAATGGGCCC ACGGGCGGCG GCCTGGGCGA AGATATTTCT GGGATCACTA | 4396 |
| ACGTCATAGT TGTGTTCCAG GATGAGATCG TCATAGGCCA TTTTTACAAA | 4446 |
| GCGCGGGCGG AGGGTGCCAG ACTGCGGTAT AATGGTTCCA TCCGGCCCAG | 4496 |

```
GGGCGTAGTT ACCCTCACAG ATTTGCATTT CCCACGCTTT GAGTTCAGAT          4546

GGGGGGATCA TGTCTACCTG CGGGGCGATG AAGAAAACGG TTTCCGGGGT          4596

AGGGGAGATC AGCTGGGAAG AAAGCAGGTT CCTGAGCAGC TGCGACTTAC          4646

CGCAGCCGGT GGGCCCGTAA ATCACACCTA TTACCGGGTG CAACTGGTAG          4696

TTAAGAGAGC TGCAGCTGCC GTCATCCCTG AGCAGGGGG CCACTTCGTT           4746

AAGCATGTCC CTGACTCGCA TGTTTTCCCT GACCAAATCC GCCAGAAGGC          4796

GCTCGCCGCC CAGCGATAGC AGTTCTTGCA AGGAAGCAAA GTTTTTCAAC          4846

GGTTTGAGAC CGTCCGCCGT AGGCATGCTT TTGAGCGTTT GACCAAGCAG          4896

TTCCAGGCGG TCCCACAGCT CGGTCACCTG CTCTACGGCA TCTCGATCCA          4946

GCATATCTCC TCGTTTCGCG GGTTGGGCG GCTTTCGCTG TACGGCAGTA           4996

GTCGGTGCTC GTCCAGACGG GCCAGGGTCA TGTCTTTCCA CGGGCGCAGG          5046

GTCCTCGTCA GCGTAGTCTG GGTCACGGTG AAGGGGTGCG CTCCGGGCTG          5096

CGCGCTGGCC AGGGTGCGCT TGAGGCTGGT CCTGCTGGTG CTGAAGCGCT          5146

GCCGGTCTTC GCCCTGCGCG TCGGCCAGGT AGCATTTGAC CATGGTGTCA          5196

TAGTCCAGCC CCTCCGCGGC GTGGCCCTTG GCGCGCAGCT TGCCCTTGGA          5246

GGAGGCGCCG CACGAGGGGC AGTGCAGACT TTTGAGGGCG TAGAGCTTGG          5296

GCGCGAGAAA TACCGATTCC GGGGAGTAGG CATCCGCGCC GCAGGCCCCG          5346

CAGACGGTCT CGCATTCCAC GAGCCAGGTG AGCTCTGGCC GTTCGGGGTC          5396

AAAAACCAGG TTTCCCCCAT GCTTTTTGAT GCGTTTCTTA CCTCTGGTTT          5446

CCATGAGCCG GTGTCCACGC TCGGTGACGA AAAGGCTGTC CGTGTCCCCG          5496

TATACAGACT TGAGAGGCCT GTCCTCGACC GATGCCCTTG AGAGCCTTCA          5546

ACCCAGTCAG CTCCTTCCGG TGGGCGCGGG GCATGACTAT CGTCGCCGCA          5596

CTTATGACTG TCTTCTTTAT CATGCAACTC GTAGGACAGG TGCCGGCAGC          5646

GCTCTGGGTC ATTTTCGGCG AGGACCGCTT TCGCTGGAGC GCGACGATGA          5696

TCGGCCTGTC GCTTGCGGTA TTCGGAATCT TGCACGCCCT CGCTCAAGCC          5746

TTCGTCACTG GTCCCGCCAC CAAACGTTTC GGCGAGAAGC AGGCCATTAT          5796

CGCCGGCATG GCGGCCGACG CGCTGGGCTA CGTCTTGCTG GCGTTCGCGA          5846

CGCGAGGCTG GATGGCCTTC CCCATTATGA TTCTTCTCGC TTCCGGCGGC          5896

ATCGGGATGC CCGCGTTGCA GGCCATGCTG TCCAGGCAGG TAGATGACGA          5946

CCATCAGGGA CAGCTTCAAG GATCGCTCGC GGCTCTTACC AGCCTAACTT          5996

CGATCACTGG ACCGCTGATC GTCACGGCGA TTTATGCCGC CTCGGCGAGC          6046

ACATGGAACG GGTTGGCATG GATTGTAGGC GCCGCCTAT ACCTTGTCTG           6096

CCTCCCCGCG TTGCGTCGCG GTGCATGGAG CCGGGCCACC TCGACCTGAA          6146

TGGAAGCCGG CGGCACCTCG CTAACGGATT CACCACTCCA AGAATTGGAG          6196

CCAATCAATT CTTGCGGAGA ACTGTGAATG CGCAAACCAA CCCTTGGCAG          6246

AACATATCCA TCGCGTCCGC CATCTCCAGC AGCCGCACGC GGCGCATCTC          6296

GGGCAGCGTT GGGTCCTGGC CACGGGTGCG CATGATCGTG CTCCTGTCGT          6346

TGAGGACCCG GCTAGGCTGG CGGGGTTGCC TTACTGGTTA GCAGAATGAA          6396

TCACCGATAC GCGAGCGAAC GTGAAGCGAC TGCTGCTGCA AAACGTCTGC          6446

GACCTGAGCA ACAACATGAA TGGTCTTCGG TTTCCGTGTT TCGTAAAGTC          6496
```

```
TGGAAACGCG GAAGTCAGCG CCCTGCACCA TTATGTTCCG GATCTGCATC      6546

GCAGGATGCT GCTGGCTACC CTGTGGAACA CCTACATCTG TATTAACGAA      6596

GCCTTTCTCA ATGCTCACGC TGTAGGTATC TCAGTTCGGT GTAGGTCGTT      6646

CGCTCCAAGC TGGGCTGTGT GCACGAACCC CCCGTTCAGC CCGACCGCTG      6696

CGCCTTATCC GGTAACTATC GTCTTGAGTC CAACCCGGTA AGACACGACT      6746

TATCGCCACT GGCAGCAGCC ACTGGTAACA GGATTAGCAG AGCGAGGTAT      6796

GTAGGCGGTG CTACAGAGTT CTTGAAGTGG TGGCCTAACT ACGGCTACAC      6846

TAGAAGGACA GTATTTGGTA TCTGCGCTCT GCTGAAGCCA GTTACCTTCG      6896

GAAAAAGAGT TGGTAGCTCT TGATCCGGCA ACAAACCAC CGCTGGTAGC       6946

GGTGGTTTTT TTGTTTGCAA GCAGCAGATT ACGCGCAGAA AAAAAGGATC      6996

TCAAGAAGAT CCTTTGATCT TTTCTACGGG GTCTGACGCT CAGTGGAACG      7046

AAAACTCACG TTAAGGGATT TTGGTCATGA GATTATCAAA AAGGATCTTC      7096

ACCTAGATCC TTTTAAATTA AAAATGAAGT TTTAAATCAA TCTAAAGTAT      7146

ATATGAGTAA ACTTGGTCTG ACAGTTACCA ATGCTTAATC AGTGAGGCAC      7196

CTATCTCAGC GATCTGTCTA TTTCGTTCAT CCATAGTTGC CTGACTCCCC      7246

GTCGTGTAGA TAACTACGAT ACGGGAGGGC TTACCATCTG GCCCCAGTGC      7296

TGCAATGATA CCGCGAGACC CACGCTCACC GGCTCCAGAT TTATCAGCAA      7346

TAAACCAGCC AGCCGGAAGG GCCGAGCGCA GAAGTGGTCC TGCAACTTTA      7396

TCCGCCTCCA TCCAGTCTAT TAATTGTTGC CGGGAAGCTA GAGTAAGTAG      7446

TTCGCCAGTT AATAGTTTGC GCAACGTTGT TGCCATTGCT GCAGGCATCG      7496

TGGTGTCACG CTCGTCGTTT GGTATGGCTT CATTCAGCTC CGGTTCCCAA      7546

CGATCAAGGC GAGTTACATG ATCCCCCATG TTGTGCAAAA AAGCGGTTAG      7596

CTCCTTCGGT CCTCCGATCG TTGTCAGAAG TAAGTTGGCC GCAGTGTTAT      7646

CACTCATGGT TATGGCAGCA CTGCATAATT CTCTTACTGT CATGCCATCC      7696

GTAAGATGCT TTTCTGTGAC TGGTGAGTAC TCAACCAAGT CATTCTGAGA      7746

ATAGTGTATG CGGCGACCGA GTTGCTCTTG CCCGGCGTCA ACACGGGATA      7796

ATACCGCGCC ACATAGCAGA ACTTTAAAAG TGCTCATCAT TGGAAAACGT      7846

TCTTCGGGGC GAAAACTCTC AAGGATCTTA CCGCTGTTGA GATCCAGTTC      7896

GATGTAACCC ACTCGTGCAC CCAACTGATC TTCAGCATCT TTTACTTTCA      7946

CCAGCGTTTC TGGGTGAGCA AAAACAGGAA GGCAAAATGC CGCAAAAAAG      7996

GGAATAAGGG CGACACGGAA ATGTTGAATA CTCATACTCT TCCTTTTTCA      8046

ATATTATTGA AGCATTTATC AGGGTTATTG TCTCATGAGC GGATACATAT      8096

TTGAATGTAT TTAGAAAAAT AAACAAATAG GGGTTCCGCG CACATTTCCC      8146

CGAAAAGTGC CACCTGACGT CTAAGAAACC ATTATTATCA TGACATTAAC      8196

CTATAAAAAT AGGCGTATCA CGAGGCCCTT TCGTCTTCAA                 8236
```

(2) INFORMATION FOR SEQ ID NO:2:

(i) SEQUENCE CHARACTERISTICS:
        (A) LENGTH: 524 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Pro Gln Ala Leu Leu Phe Val Pro Leu Leu Val Phe Pro
 1               5                  10                  15

Leu Cys Phe Gly Lys Phe Pro Ile Tyr Thr Ile Leu Asp Lys Leu
                20                  25                  30

Gly Pro Trp Ser Pro Ile Asp Ile His His Leu Ser Cys Pro Asn
                35                  40                  45

Asn Leu Val Val Glu Asp Glu Gly Cys Thr Asn Leu Ser Gly Phe
                50                  55                  60

Ser Tyr Met Glu Leu Lys Val Gly Tyr Ile Leu Ala Ile Lys Met
                65                  70                  75

Asn Gly Phe Thr Cys Thr Gly Val Val Thr Glu Ala Glu Thr Tyr
                80                  85                  90

Thr Asn Phe Val Gly Tyr Val Thr Thr Thr Phe Lys Arg Lys His
                95                 100                 105

Phe Arg Pro Thr Pro Asp Ala Cys Arg Ala Ala Tyr Asn Trp Lys
               110                 115                 120

Met Ala Gly Asp Pro Arg Tyr Glu Glu Ser Leu His Asn Pro Tyr
               125                 130                 135

Pro Asp Tyr Arg Trp Leu Arg Thr Val Lys Thr Thr Lys Glu Ser
               140                 145                 150

Leu Val Ile Ile Ser Pro Ser Val Ala Asp Leu Asp Pro Tyr Asp
               155                 160                 165

Arg Ser Leu His Ser Arg Val Phe Pro Ser Gly Lys Cys Ser Gly
               170                 175                 180

Val Ala Val Ser Ser Thr Tyr Cys Ser Thr Asn His Asp Tyr Thr
               185                 190                 195

Ile Trp Met Pro Glu Asn Pro Arg Leu Gly Met Ser Cys Asp Ile
               200                 205                 210

Phe Thr Asn Ser Arg Gly Lys Arg Ala Ser Lys Gly Ser Glu Thr
               215                 220                 225

Cys Gly Phe Val Asp Glu Arg Gly Leu Tyr Lys Ser Leu Lys Gly
               230                 235                 240

Ala Cys Lys Leu Lys Leu Cys Gly Val Leu Gly Leu Arg Leu Met
               245                 250                 255

Asp Gly Thr Trp Val Ala Met Gln Thr Ser Asn Glu Thr Lys Trp
               260                 265                 270

Cys Pro Pro Asp Gln Leu Val Asn Leu His Asp Phe Arg Ser Asp
               275                 280                 285

Glu Ile Glu His Leu Val Val Glu Glu Leu Val Arg Lys Arg Glu
               290                 295                 300

Glu Cys Leu Asp Ala Leu Glu Ser Ile Met Thr Thr Lys Ser Val
               305                 310                 315

Ser Phe Arg Arg Leu Ser His Leu Arg Lys Leu Val Pro Gly Phe
               320                 325                 330

Gly Lys Ala Tyr Thr Ile Phe Asn Lys Thr Leu Met Glu Ala Asp
               335                 340                 345

Ala His Tyr Lys Ser Val Arg Thr Trp Asn Glu Ile Leu Pro Ser
               350                 355                 360

Lys Gly Cys Leu Arg Val Gly Gly Arg Cys His Pro His Val Asn
               365                 370                 375
```

```
Gly Val Phe Phe Asn Gly Ile Ile Leu Gly Pro Asp Gly Asn Val
                380                 385                 390

Leu Ile Pro Glu Met Gln Ser Ser Leu Leu Gln Gln His Met Glu
                395                 400                 405

Leu Leu Glu Ser Ser Val Ile Pro Leu Val His Pro Leu Ala Asp
                410                 415                 420

Pro Ser Thr Val Phe Lys Asp Gly Asp Glu Ala Glu Asp Phe Val
                425                 430                 435

Glu Val His Leu Pro Asp Val His Asn Gln Val Ser Gly Val Asp
                440                 445                 450

Leu Gly Leu Pro Asn Trp Gly Lys Tyr Val Leu Leu Ser Ala Gly
                455                 460                 465

Ala Leu Thr Ala Leu Met Leu Ile Ile Phe Leu Met Thr Cys Cys
                470                 475                 480

Arg Arg Val Asn Arg Ser Glu Pro Thr Gln His Asn Leu Arg Gly
                485                 490                 495

Thr Gly Arg Glu Val Ser Val Thr Pro Gln Ser Gly Lys Ile Ile
                500                 505                 510

Ser Ser Trp Glu Ser His Lys Ser Gly Gly Glu Thr Arg Leu
                515                 520
```